US011293910B2

(12) United States Patent
Benfey et al.

(10) Patent No.: US 11,293,910 B2
(45) Date of Patent: Apr. 5, 2022

(54) METHODS AND DEVICES FOR NON-INVASIVE ROOT PHENOTYPING

(71) Applicant: Hi Fidelity Genetics, Inc., Durham, NC (US)

(72) Inventors: Philip Benfey, Durham, NC (US); Jesse Windle, Durham, NC (US); Daniel Goldman, Durham, NC (US); Jeffrey Aguilar, Durham, NC (US); Logan Johnson, Durham, NC (US)

(73) Assignee: Hi Fidelity Genetics, Inc., Durham, NC (US)

( * ) Notice: Subject to any disclaimer, the term of this patent is extended or adjusted under 35 U.S.C. 154(b) by 0 days.

(21) Appl. No.: 16/938,822

(22) Filed: Jul. 24, 2020

(65) Prior Publication Data

US 2021/0172922 A1 Jun. 10, 2021

Related U.S. Application Data

(63) Continuation of application No. 15/778,195, filed as application No. PCT/US2016/063417 on Nov. 22, 2016, now Pat. No. 10,761,074.

(Continued)

(51) Int. Cl.
*G01R 27/26* (2006.01)
*G01N 33/00* (2006.01)
(Continued)

(52) U.S. Cl.
CPC ......... *G01N 33/0098* (2013.01); *G01N 27/04* (2013.01); *G01N 27/226* (2013.01);
(Continued)

(58) Field of Classification Search
CPC .... G01R 27/2605; G01R 27/02; G01R 27/22; G01R 27/26; G01R 31/2837; G01R 35/00; G01R 15/06; G01R 15/142
(Continued)

(56) References Cited

U.S. PATENT DOCUMENTS 7,956,624 B2   6/2011   Beaulieu
9,030,549 B2   5/2015   Redden
(Continued)

FOREIGN PATENT DOCUMENTS

CN    102565150 A   7/2012
WO    2007128122 A1   11/2007

OTHER PUBLICATIONS

Amato, M et al. (2009). "Multi-Electrode 3D Resistivity Imaging of Alfalfa Root Zone," European Journal of Agronomy 31(4):213-222.
(Continued)

*Primary Examiner* — Raul J Rios Russo
(74) *Attorney, Agent, or Firm* — Morrison & Foerster LLP

(57) ABSTRACT

The present disclosure provides for an electronic sensor for detecting a root of a plant in soil, the electronic sensor that includes a first conductor plate configured to be disposed in soil, a switch, a power supply, and signal extractor. The switch is electrically coupled to the first conductor plate and is configured to switch between a first mode and a second mode. The power supply is electrically coupled to the switch and is configured to provide an electrical charge to the first conductor plate in the first mode of the switch. The signal extractor is electrically coupled to the switch and is configured to extract a signal response at the first conductor plate in the second mode of the switch. The present disclosure further provides a second conductor plate configured to be disposed in soil adjacent to and substantially parallel to the first conductor plate. The second conductor plate is electrically coupled to ground.

28 Claims, 13 Drawing Sheets

Related U.S. Application Data

(60) Provisional application No. 62/259,587, filed on Nov. 24, 2015.

(51) Int. Cl.

| | |
|---|---|
| *G01R 27/02* | (2006.01) |
| *G01R 27/22* | (2006.01) |
| *G01R 31/28* | (2006.01) |
| *G01R 35/00* | (2006.01) |
| *G01R 15/06* | (2006.01) |
| *G01R 15/14* | (2006.01) |
| *G01N 27/04* | (2006.01) |
| *G01N 27/22* | (2006.01) |
| *A01G 7/00* | (2006.01) |

(52) U.S. Cl.
CPC ............ *G01R 15/06* (2013.01); *G01R 15/142* (2013.01); *G01R 27/02* (2013.01); *G01R 27/22* (2013.01); *G01R 27/26* (2013.01); *G01R 27/2605* (2013.01); *G01R 31/2837* (2013.01); *G01R 35/00* (2013.01); *A01G 7/00* (2013.01); *G01N 27/22* (2013.01)

(58) Field of Classification Search
USPC .......... 324/76.11–76.83, 459, 600, 606, 647, 324/649, 656, 658, 663, 672, 679, 705
See application file for complete search history.

(56) References Cited

U.S. PATENT DOCUMENTS

| | | | |
|---|---|---|---|
| 9,064,173 | B2 | 6/2015 | Redden |
| 10,761,074 | B2 | 9/2020 | Benfey et al. |
| 2006/0139037 | A1 | 6/2006 | Hughes |
| 2006/0144438 | A1* | 7/2006 | Dresselhaus ........ F16K 37/0091 137/78.3 |
| 2009/0293354 | A1 | 12/2009 | Goldberg et al. |
| 2009/0322357 | A1 | 12/2009 | Beaulieu |
| 2011/0036155 | A1 | 2/2011 | Dresselhaus et al. |
| 2012/0091222 | A1 | 4/2012 | Dresselhaus et al. |
| 2015/0015697 | A1 | 1/2015 | Redden et al. |
| 2015/0027040 | A1 | 1/2015 | Redden |
| 2015/0027041 | A1 | 1/2015 | Redden |
| 2015/0027043 | A1 | 1/2015 | Redden |
| 2015/0027044 | A1 | 1/2015 | Redden |
| 2015/0237790 | A1 | 8/2015 | Redden et al. |
| 2015/0323491 | A1 | 11/2015 | Miller et al. |
| 2016/0018799 | A1 | 1/2016 | Gettings et al. |
| 2016/0019780 | A1 | 1/2016 | Gettings et al. |
| 2016/0050902 | A1* | 2/2016 | Crisp ................. G01N 33/24 43/124 |
| 2017/0202202 | A1* | 7/2017 | Crisp ................. A01M 19/00 |
| 2018/0348186 | A1 | 12/2018 | Benfey et al. |

OTHER PUBLICATIONS

Araus, J.L. et al. (Jan. 2014). "Field High-Throughput Phenotyping: The New Crop Breeding Frontier," Trends in Plant Science 19(1):52-61.

Dalton, F.N. (1995). "In-Situ Root Extent Measurements by Electrical Capacitance Methods," Plant and Soil 173(1):157-165.

Extended European Search Report received for European Patent Application No. 16869197.0, dated Jun. 28, 2019, 8 pages.

Hessel, D.A. (2014). "Deciphering the Genetic Architecture of Native Resistance and Tolerance to Western Corn Rootworm Larval Feeding", Graduate Theses and Dissertations, Iowa State University, 211 pages.

Ho, M.D. et al. (2004). "Optimization Modeling of Plant Root Architecture for Water and Phosphorus Acquisition," Journal of Theoretical Biology 226:331-340.

International Preliminary Report on Patentability dated Jun. 7, 2018, for PCT Application No. PCT/US16/63417, filed on Nov. 22, 2016, 10 pages.

International Search Report and Written Opinion dated Mar. 27, 2017, for PCT Application No. PCT/US16/63417 filed on Nov. 22, 2016, 13 pages.

Kuijken, R.C.P. et al. (2015). "Root Phenotyping: From Component Trait in the Lab to Breeding," Journal of Experimental Botany 66(18):5389-5401.

Penn State College. (2015). "Maize Shovelomics," Plant Science, Available Online athttps://plantscience.psu.edu/research/labs/roots/methods/field/shovelomics/shovelo mies, Retrieved on Jul. 9, 2015, pp. 1-3.

Uga, Y. et al. (2013). "Control of Root System Architecture by Deeper Rooting 1 Increases Rice Yield under Drought Conditions," Nature Genetics 45(9):1-9.

Van Beem, J. et al. (July-Aug. 1998). "Estimating Root Mass in Maize using A Portable Capacitance Meter," Agronomy Journal 90(4):566-570.

York, L.M. et al. (2015, e-pub. Jun. 3, 2015). "Intensive Field Phenotyping of Maize (*Zea mays* L.) Root Crowns dentifies Phenes and Phene Integration Associated with Plant Growth and Nitrogen Acquisition," Journal of Experimental Botany 66(18):5493-5505.

* cited by examiner

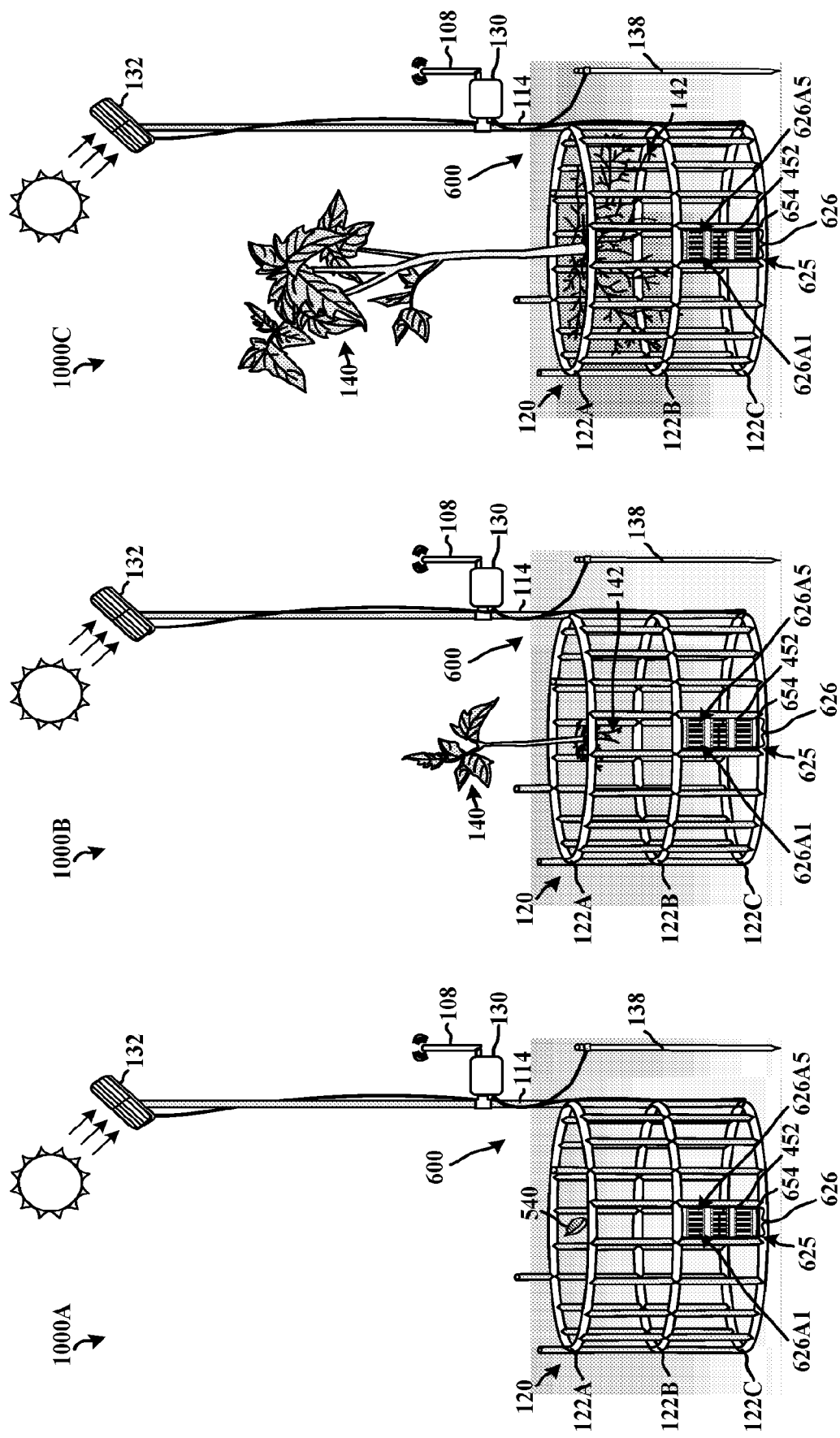

METHODS AND DEVICES FOR NON-INVASIVE ROOT PHENOTYPING

CROSS-REFERENCE TO RELATED APPLICATIONS

The present application is a continuation of U.S. patent application Ser. No. 15/778,195, filed on May 22, 2018, which is a U.S. National Phase patent application of PCT/US2016/063417, filed Nov. 22, 2016, which claims priority to Provisional Application No. 62/259,587, entitled "METHODS AND DEVICES FOR NON-INVASIVE ROOT PHENOTYPING," filed Nov. 24, 2015, the disclosures of which are hereby incorporated by reference in their entirety.

STATEMENT OF GOVERNMENT SUPPORT

This invention was made with Government support under Grant No. DE-AR0000725 awarded by the Advanced Research Projects Agency-Energy (ARPA-E), U.S. Department of Energy. The Government has certain rights in this invention.

BACKGROUND

Field

The present disclosure generally relates to devices for non-invasive root phenotyping and more specifically to an electronic system and electronic devices to detect plant roots, as well as monitor plant root traits over time.

Description of Related Art

Root system architecture (RSA) describes the spatial arrangement of roots within the soil that is shaped by genetic and environmental factors. The RSA impacts plant fitness, crop performance, grain yield, and can influence a plant's drought tolerance and ability to acquire nutrients. For example, studies have shown that modifying a single gene, DEEPER ROOTING 1 (DRO1), in rice changes the root angle without changing the overall length of the root. This slight change in root angle directs the roots downward, which provides the plant with more access to groundwater. As such, the modified rice (e.g., rice with the DRO1 gene) yields 10% less under drought conditions, whereas unmodified rice (e.g., rice without the DRO1 gene) yields 60% less under the same conditions as compared to well-watered conditions.

Root traits rarely have been applied to breeding programs due, in part, to the difficulty in measuring and monitoring root growth in opaque and complex soils. Current techniques either reduce crop yield or interfere with the plants growing cycle. One technique, for example, uproots field-grown plants for a single time-point measurement. Not only is this technique destructive, but the uprooting process changes in situ factors (e.g., removes the soil foundation), which can bias the measurements (e.g., root angle measurements without soil).

A less destructive technique provides a viewing window such as a rhizotron to observe the roots over time. This technique places a transparent barrier in the path of root growth in order to view the roots that grow adjacent the viewing window of the rhizotron camera. This technique interferes with the plant's natural growing cycle, as it intentionally places an obstruction in the natural path of root development.

Real-time monitoring of the RSA during the growing season without interfering with the plant's growing cycle can provide invaluable information that can be used to produce healthier plants and yield a more abundant crop. As such, a challenge exists for improved, non-invasive techniques for monitoring root phenotypes, such as growth rate, length, angle, and the like.

BRIEF SUMMARY

The following presents a simplified summary of one or more aspects in order to provide a basic understanding of such examples. This summary is not an extensive overview of all contemplated examples, and it is intended to neither identify key or critical elements of all examples nor delineate the scope of any or all examples. Its purpose is to present some concepts of one or more examples in a simplified form as a prelude to the more detailed description that is presented below.

In some examples, the present disclosure provides an electronic sensor for detecting a root of a plant in soil, the electronic sensor comprising: a first conductor plate configured to be disposed in soil; a switch electrically coupled to the first conductor plate, wherein the switch is configured to switch between a first mode and a second mode; a power supply electrically coupled to the switch, wherein the power supply is configured to provide an electrical charge to the first conductor plate in the first mode of the switch; and a signal extractor electrically coupled to the switch, wherein the signal extractor is configured to extract a signal response at the first conductor plate in the second mode of the switch. In certain examples, the present disclosure further provides a second conductor plate configured to be disposed in soil adjacent to and substantially parallel to the first conductor plate, wherein the second conductor plate is electrically coupled to ground.

In some examples, the present disclosure provides an electronic device for monitoring growth of a root of a plant in a soil location, comprising: a support structure suitable for arrangement adjacent to the soil location; and a plurality of electronic sensors affixed to the support structure, wherein at least one electronic sensor of the plurality of electronic sensors comprises: a first conductor plate configured to be disposed in soil; a switch electrically coupled to the first conductor plate, wherein the switch is configured to switch between a first mode and a second mode; a power supply electrically coupled to the switch, wherein the power supply is configured to provide an electrical charge to the first conductor plate in the first mode of the switch; and a signal extractor electrically coupled to the switch, wherein the signal extractor is configured to extract a signal response at the first conductor plate in the second mode of the switch. In certain examples, the present disclosure further provides a second conductor plate configured to be disposed in soil adjacent to and substantially parallel to the first conductor plate, wherein the second conductor plate is electrically coupled to ground.

In some examples, the present disclosure provides a method for monitoring growth of a plant root through use of an electronic device comprising one or more processors, memory, and a plurality of sensors positioned around the plant root, the method comprising: electrically charging, at a sensor among the plurality of sensors, a first conductor plate configured to be disposed in soil from a power supply over a first predetermined time; electrically uncoupling the first conductor plate from the power supply; extracting a signal response at the first conductor plate over a second predetermined time; determining whether a portion of the signal response exceeds a threshold value, wherein a root presence is associated with a determination that the portion of the signal response exceeded the threshold value; and storing a root presence indicator to the memory in accordance with the portion of the signal response exceeding the threshold value. In certain examples, the present disclosure further provides for electrically grounding a second conductor plate, wherein the second conductor plate is configured to be disposed in soil and adjacent to and substantially parallel to the first conductor plate.

In some examples, the present disclosure provides a non-transitory computer-readable storage medium comprising one or more programs for execution by one or more processors of an electronic device, the one or more programs including instructions which, when executed by the one or more processors, cause the device to: electrically charge, at a sensor among the plurality of sensors, a first conductor plate configured to be disposed in soil from a power supply over a first predetermined time; electrically uncouple the first conductor plate from the power supply; extract a signal response at the first conductor plate over a second predetermined time; determine whether a portion of the signal response exceeds a threshold value, wherein a root presence is associated with a determination that the portion of the signal response exceeded the threshold value; and store a root presence indicator to a memory in accordance with the portion of the signal response exceeding the threshold value. In certain examples, the present disclosure further provides for electrically grounding a second conductor plate, wherein the second conductor plate is configured to be disposed in soil and adjacent to and substantially parallel to the first conductor plate.

In some examples, the present disclosure provides a device for monitoring growth of a plant root, comprising: a cage structure suitable for arrangement around the plant root; a plurality of root sensors affixed to the cage structure, wherein each root sensor of the plurality is configured to detect the presence of the plant root; one or more processors configured to receive data from the plurality of root sensors; and a power source coupled to the one or more processors and the plurality of root sensors.

In some examples, the present disclosure provides a non-transitory computer-readable storage medium comprising one or more programs for execution by one or more processors of an electronic device, the one or more programs including instructions which, when executed by the one or more processors, cause the device to: receive data representing an input from a root sensor of a plurality of root sensors, wherein the input is from a plant root of a plant in a soil location, and wherein the plurality of root sensors is positioned around the soil location; and determine a growth characteristic of the plant root based on the data.

In some examples, the present disclosure provides a method for monitoring growth of a plant root by a device comprising one or more processors and a plurality of root sensors positioned around the plant root, the method comprising: receiving data representing an input from a root sensor of the plurality, wherein the input is from the plant root; and determining a growth characteristic of the plant root based on the data.

In some examples, the present disclosure provides a device comprising: a plurality of root sensors; one or more processors; a memory; and one or more programs, wherein the one or more programs are stored in the memory and configured to be executed by the one or more processors, the one or more programs including instructions for: receiving data representing an input from a root sensor of the plurality, wherein the input is from a plant root; and determining a growth characteristic of the plant root based on the data.

In some examples, the present disclosure provides a method for monitoring growth of a plant root, comprising: positioning a plurality of root sensors around a soil location; planting a seed in the soil location; after the seed has grown into a plant having a plant root, receiving data representing an input from a root sensor of the plurality, wherein the input is from the plant root; and determining a growth characteristic of the plant root based on the data.

In some examples, the present disclosure provides a method for monitoring growth of a plant root, comprising: positioning a plurality of root sensors around a soil location, wherein a plant producing a plant root is planted in the soil location; receiving data representing an input from a root sensor of the plurality, wherein the input is from the plant root; and determining a growth characteristic of the plant root based on the data.

In some examples, the present disclosure provides a method for selecting a plant for breeding based on a root growth characteristic, comprising: positioning a plurality of root sensors around a soil location; planting a seed in the soil location; after the seed has grown into a plant having a plant root, receiving data representing an input from a root sensor of the plurality, wherein the input is from the plant root; determining a root growth characteristic of the plant root based on the data; and selecting the plant for breeding based on the determined root growth characteristic.

In some examples, the present disclosure provides a method for determining an effect of a plant-microbe interaction on a root growth characteristic, comprising: positioning a plurality of root sensors around a soil location; planting a first seed in the soil location; inoculating the soil location with a first microbe or community of microbes; after the first seed has grown into a first plant having a first plant root, and after a plant-microbe interaction is established between the first plant and the first microbe: receiving data representing an input from a root sensor of the plurality, wherein the input is from the first plant root; determining a first root growth characteristic of the first plant root based on the data; determining a reference root growth characteristic of a reference plant root from a reference plant of the same species as the first plant; and determining the effect of the plant-microbe interaction on the first root growth characteristic by comparing the first root growth characteristic to the reference root growth characteristic.

In some examples, the present disclosure provides a method for determining an effect of a plant-microbe interaction on a root growth characteristic, comprising: positioning a plurality of root sensors around a soil location; inoculating a first seed with a first microbe or community of microbes; planting the first seed in the soil location; after the first seed has grown into a first plant having a first plant root, and after a plant-microbe interaction is established between the first plant and the first microbe or community of microbes: receiving data representing an input from a root sensor of the plurality, wherein the input is from the first plant root; determining a first root growth characteristic of the first plant root based on the data; determining a reference root growth characteristic of a reference plant root from a reference plant of the same species as the first plant; and determining the effect of the plant-microbe interaction on the first root growth characteristic by comparing the first root growth characteristic to the reference root growth characteristic.

In some examples, the present disclosure provides a method for monitoring a soil organism, comprising: positioning a plurality of root sensors around a soil location; planting a seed in the soil location; after the seed has grown into a plant having a plant root, and after the soil organism has invaded the soil location, receiving data representing an input from a root sensor of the plurality; based on the data, determining whether the input is from the plant root or the soil organism; and in accordance with a determination that the input is from the soil organism: monitoring the soil organism based on the data.

In some examples, the present disclosure provides a method for monitoring a soil organism, comprising: positioning a plurality of root sensors around a soil location, wherein a plant having a plant root is planted in the soil location, and wherein the soil organism has invaded the soil location; receiving data representing an input from a root sensor of the plurality; based on the data, determining whether the input is from the plant root or the soil organism; and in accordance with a determination that the input is from the soil organism: monitoring the soil organism based on the data.

It is to be understood that one, some, or all of the properties of the various examples described above and herein may be combined to form other examples of the present invention. These and other aspects of the invention will become apparent to one of skill in the art. These and other examples of the invention are further described by the detailed description that follows.

BRIEF DESCRIPTION OF THE FIGURES

For a better understanding of the various described examples, reference should be made to the description below, in conjunction with the following figures in which like reference numerals refer to corresponding parts throughout the figures.

FIGS. 10A-10C are diagrams illustrating an example of a non-invasive root phenotyping device with a plurality of proximity sensors surrounding a plant at various stages of growth of a plant root system over time.

DETAILED DESCRIPTION

Figure 1:
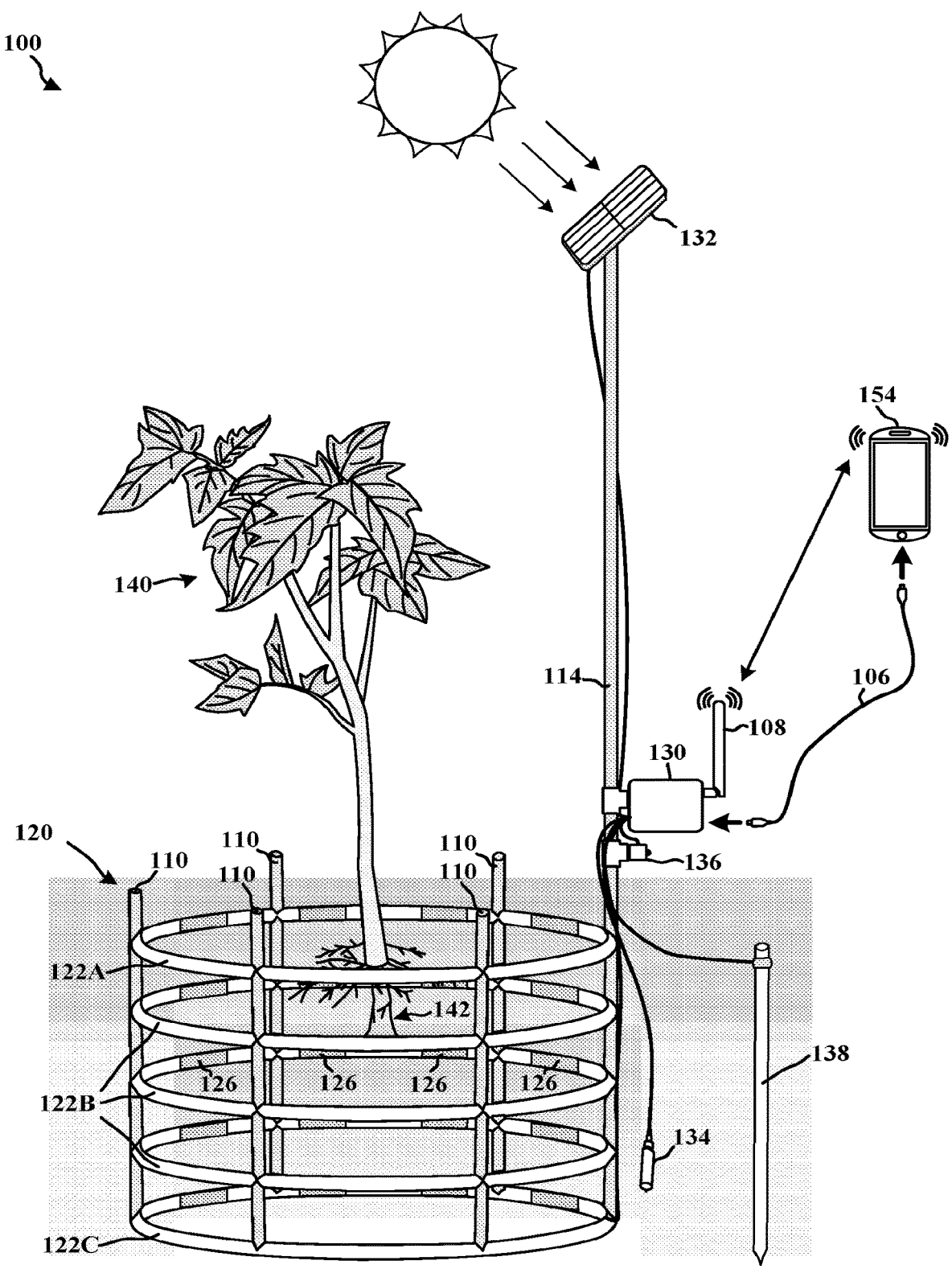
FIG. 1 is a diagram illustrating an example of a non-invasive root phenotyping device.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well-known structures and components are shown in block diagram form in order to avoid obscuring such concepts.

Examples of detecting roots for monitoring growth of a plant root will now be presented with reference to various electronic devices and methods. These electronic devices and methods will be described in the following detailed description and illustrated in the accompanying drawing by various blocks, components, circuits, steps, processes, algorithms, etc. (collectively referred to as "elements"). These elements may be implemented using electronic hardware, computer software, or any combination thereof. Whether such elements are implemented as hardware or software depends upon the particular application and design constraints imposed on the overall system.

By way of example, an element, any portion of an element, or any combination of elements may be implemented using one or more processors. Examples of processors include microprocessors, microcontrollers, graphics processing units (GPUs), central processing units (CPUs), application processors, digital signal processors (DSPs), reduced instruction set computing (RISC) processors, systems on a chip (SoC), baseband processors, field programmable gate arrays (FPGAs), programmable logic devices (PLDs), state machines, gated logic, discrete hardware circuits, and other suitable hardware configured to perform the various functionality described throughout this disclosure. One or more processors in the processing system may execute software. Software shall be construed broadly to mean instructions, instruction sets, code, code segments, program code, programs, subprograms, software components, applications, software applications, software packages, routines, subroutines, objects, executables, threads of execution, procedures, functions, etc., whether referred to as software, firmware, middleware, microcode, hardware description language, or otherwise.

Accordingly, in one or more examples, the functions described may be implemented in hardware, software, or any combination thereof. If implemented in software, the functions may be stored on or encoded as one or more instructions or code on a computer-readable medium. Computer-readable media may include transitory or non-transitory computer storage media for carrying or having computer-executable instructions or data structures stored thereon. Both transitory and non-transitory storage media may be any available media that can be accessed by a computer as part of the processing system. By way of example, and not limitation, such computer-readable media can comprise a random-access memory (RAM), a read-only memory (ROM), an electrically erasable programmable ROM (EEPROM), optical disk storage, magnetic disk storage, other magnetic storage devices, combinations of the aforementioned types of computer-readable media, or any other medium that can be used to store computer executable code in the form of instructions or data structures that can be accessed by a computer. Further, when information is transferred or provided over a network or another communications connection (hardwired, wireless, cellular, or combination thereof) to a computer, the computer or processing system properly determines the connection as a transitory or non-transitory computer-readable medium, depending on the particular medium. Thus, any such connection is properly termed a computer-readable medium. Combinations of the above should also be included within the scope of the computer-readable media. Non-transitory computer-readable media excludes signals per se and the air interface.

The present disclosure provides for an electronic device to detect and/or monitor the growth of a plant root. The electronic device includes a support structure (e.g., cage structure) suitable for arrangement adjacent to the soil location. The electronic device further includes a plurality of electronic sensors trellised to the support structure. Some of the plurality of electronic sensors are root contact sensors and some are root proximity sensors. The root contact sensor includes a switch electrically coupled to a first conductor plate (e.g., contact sensor), a signal extractor (e.g., voltage divider, analog to digital converter), and a power supply (e.g., voltage or current source). The switch is configured to electrically couple the power supply to the first conductor plate in a first mode and electrically couple the signal extractor to the first conductor plate in a second mode.

In the second mode, the signal extractor receives a signal response from the first conductor plate after being charged by the power source in the first mode. A microcontroller receives signal response and compares it with baseline signal responses stored in memory. In instances where a root is not physically touching the first conductor plate, the signal response from the first conductor plate is characteristic of the baseline signal response for no root impinging on the first conductor plate. In instances where a root is physically touching the first conductor plate, the signal response from the first conductor plate is characteristic of the baseline signal response for a root impinging on the first conductor plate.

The root proximity sensor includes a first conductor plate and a second conductor plate, which is electrically coupled to ground. The proximity sensor is a switch electrically coupled to a first conductor plate, a signal extractor (e.g., voltage divider, analog to digital converter), and a power supply (e.g., voltage or current source). The switch of the proximity sensor is configured to electrically couple the power supply to the first conductor plate in a first mode and electrically couple the signal extractor to the first conductor plate in a second mode.

For the root proximity sensor, the first conductor plate and the second conductor plate are substantially parallel and electrically coupled through the impedance of the soil. Perturbations in the impedance in the soil between the first conductor plate and the second conductor plate cause a signal response at the first conductor plate when the switch is in the second mode. A microcontroller receives the signal response from the signal extractor and compares it with baseline signal responses stored in memory. In instances where a root is not physically between the first conductor plate and the second conductor plate, the signal response from the first conductor plate is characteristic of the baseline signal response for no root between the first conductor plate and the second conductor plate. In instances where a root is physically between the first conductor plate and the second conductor plate, the signal response from the first conductor plate is characteristic of the baseline signal response for a root between the first conductor plate and the second conductor plate. In instances where a root is physically touching the first conductor plate, the signal response from the first conductor plate is characteristic of the baseline signal response for a root impinging on the first conductor plate.

The electronic sensors and devices of the present disclosure implement techniques of non-invasive root phenotyping, such as the techniques for monitoring growth of a plant root, techniques for selecting a plant for breeding based on a root growth characteristic, techniques for determining an effect of a plant-microbe interaction on a root growth characteristic, and/or techniques for monitoring a soil organism. These techniques described herein provide for monitoring of plant root growth in situ while the plant is growing, provide for a higher resolution of monitoring of RSA than existing devices (e.g., mini-rhizotron), and provide for a low-cost solution that is suitable for field use with minimal interference to plant growth.

FIG. 1 is a diagram illustrating an example of a non-invasive root phenotyping device 100. The root phenotyping device 100 includes a support structure suitable for arrangement in a soil location adjacent a plant 140. In this example, the support structure is a cage structure 120 with top circular support 122A, middle circular supports 122B, and bottom circular supports 122C vertically connected to extended vertical support 114 and vertical supports 110 that form a backbone for the support structure.

It is contemplated that additional circular supports 122A, 122B, 122C can be added to a desired cage structure 120. For example, a cage structure can include 1 or more, 2 or more, 3 or more, 4 or more, 5 or more, 6 or more, 7 or more, 8 or more, 9 or more, 10 or more, 11 or more, or 12 or more, etc. circular supports 122A, 122B, 122C. The number of circular supports 122A, 122B, 122C to be used can be influenced by, for example, a desired spacing and/or density of the cage circular supports 122A, 122B, 122C; a size, shape, and/or complexity of the RSA to be monitored; the shape and/or configuration of the device; a number of inputs that may be accommodated by a microcontroller of the present disclosure; and so forth. Likewise, the cage structure 120 can be an auger or include a helical blade affixed to the cage structure 102 to facilitate burrowing the cage structure 120 into the soil around the plant 140.

In some examples, the cage structure 120 is made from any material that resists deformation upon insertion into a desired soil type without affecting the health and growth of the plant 140. For example, the cage structure 120 material can be metals (e.g., galvanized steel, stainless steel), plastic (e.g., bioplastics), and the like. In some examples, the cage structure 120 is made from biodegradable and/or compostable material such as polylactic acid (PLA), poly-3-hydroxybutyrate (PHB), polyhydroxyalkanoates (PHA), and the like. In some instances, a 3-D printer can be utilized to construct the cage structure 120 using a suitable thermoplastic (e.g., PLA, etc.). In some instances, the cage structure 120 can be injected molded using a suitable thermoplastic (e.g., PLA, etc.).

The root phenotyping device 100 further includes a plurality of conductor plates 126 affixed to the support structure (e.g., cage structure 120). For example, the plurality of conductor plates 126 can be trellised to a top circular support 122A, a middle circular support 122B, and a bottom circular support 122C, as depicted in FIG. 1. In some instances, the plurality of conductor plates 126 can be trellised to the extended vertical support 114 and vertical supports 110 that provides for a relatively fixed position during insertion into a soil location and subsequent operation. In some instances, one or more of the plurality of conductor plates 126 can be provided on a mesh and positioned between the vertical supports 110 and the circular supports 122A, 122B, 122C. Each of the plurality of conductor plates 126 is electrically coupled (e.g., via wired interconnects) to a controller 130 (e.g., microcontroller) that is configured to determine whether a root physically touches a contact sensor.

As depicted in FIG. 1, the root phenotyping device 100 includes an electrode 138 that is electrically coupled to the controller 130. Electrode 138 is an electrically conductive rod that is inserted into the soil to provide a good electrical coupling to earth ground. In some examples, the electrode 138 is made from a non-reactive metal (e.g., stainless steel) or a highly conductive metal (e.g., copper).

In some examples, at least one of the plurality of conductor plates 126 is a part of a root sensor that is configured to detect a change in impedance between soil and a root caused by physical contact with a root 142 of plant 140. In some instances, the root sensor detects a change in capacitance between the soil and at least one of the plurality of conductor plates 126 once a root 142 physically contacts at least one of the plurality of conductor plates 126. In some instances, the root sensor detects a change in resistance between the soil and at least one of the plurality of conductor plates 126 once a root 142 physically contacts the at least one of the plurality of conductor plates 126.

As depicted in FIG. 1, controller 130 includes a communications unit (e.g., antenna 108, I/O port for cable 106) configured to transmit sensory data to a mobile device 154 (e.g., smart phone, tablet PC). In some instances, the communications unit can transmit sensory data over cable 106 to a mobile device 154. In some instances, cable 106 is a serial cable with appropriate connectors to interface with the communication unit of controller 130 and the mobile device 154. In such an instance, the communication unit includes circuitry (e.g., serial transceiver, etc.) to transmit and receive serial communications. In some examples, the communications unit can include an antenna 108 and circuitry configured to transmit sensory data wirelessly (e.g., Bluetooth, WiFi) to mobile device 154. In such an instance, the communication unit includes circuitry (e.g., Bluetooth transceiver, WiFi transceiver, etc.) to transmit and receive serial communications via wireless protocols. In some examples, the communications unit can include an antenna 108 and circuitry configured to transmit sensory data over a cellular network (e.g., 3G, 4G, LTE) to cellular tower or mobile device 154. In such an instance, the communication unit includes circuitry (e.g., 3G transceiver, 4G transceiver, LTE transceiver, etc.) to transmit and receive communications via cellular protocols.

The root phenotyping device 100 can also include one or more sensors (e.g., soil sensor 134, ambient sensor 136) associated with any desired aspect of plant 140, the soil location, and/or one or more above-ground conditions at or near the soil location. In general, the soil sensor 134 is located within the soil or at the air/soil interface, and the ambient sensor 136 is located above the soil or at the air/soil interface. For example, the soil sensor 134 can be configured to determine one or more nutrient levels (e.g., phosphorus, nitrogen, oxygen, soil humidity, temperature, moisture, pH, etc.) of the soil situated at or near the plant location. In some instances, soil sensor 134 is a nutrient sensor. In some instances, soil sensor 134 is a soil humidity sensor, a moisture sensor, or a temperature sensor.

The ambient sensor 136 is configured to determine one or more environmental/ambient conditions above ground. In some examples, the ambient sensor 136 is configured to determine one or more environmental conditions (e.g., humidity, temperature, light, etc.) associated with the plant. In some instances, the ambient sensor 136 is a temperature sensor or a humidity sensor. In some instances, the ambient sensor 136 is a rain sensor or a light sensor. Both the soil sensor 134 and the ambient sensor 136 provide in situ information regarding localized field locations (e.g., related to soil desiccation and/or fertilizer retention). This information assists breeders and growers in targeting irrigation and/or fertilizer to specific field locations, which provides cost and energy savings.

Power provided to controller 130 of the root phenotyping device 100 includes one or more power sources. For example, as depicted in FIG. 1, the root phenotyping device 100 can include solar cell 132 affixed to extended vertical support 114 to provide electrical power to controller 130. Other suitable power sources can include one or more solar cells, one or more batteries, or any combination thereof (e.g., solar cell 132 configured to charge a battery). In some examples, controller 130 of the present disclosure has both active and power-down modes, which provide for modulation of power consumption.

Figure 2A:
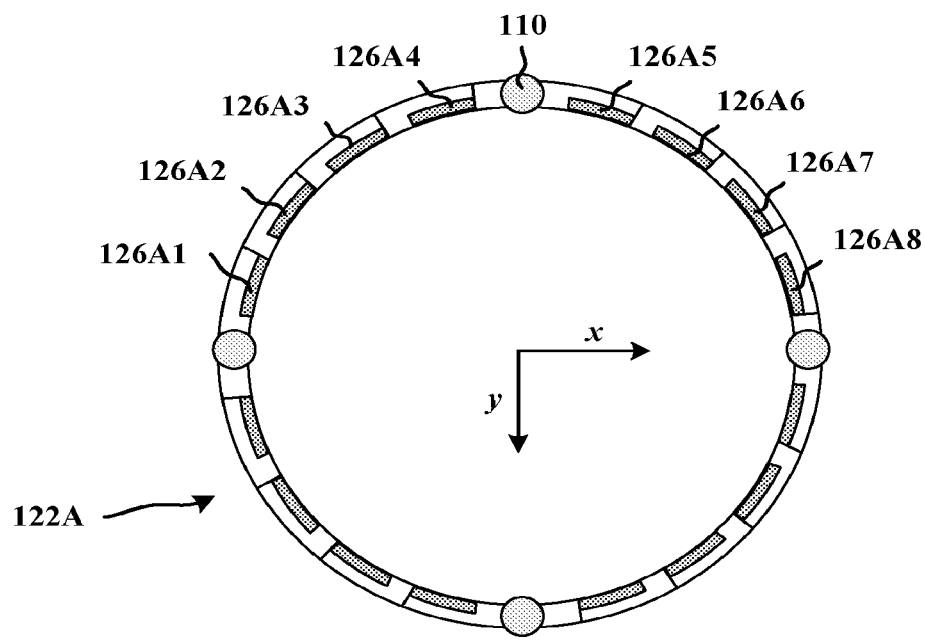
FIGS. 2A and 2B are diagrams illustrating a top-view and an ISO-view of a non-invasive root phenotyping device with conductor plates.
Figure 2B:
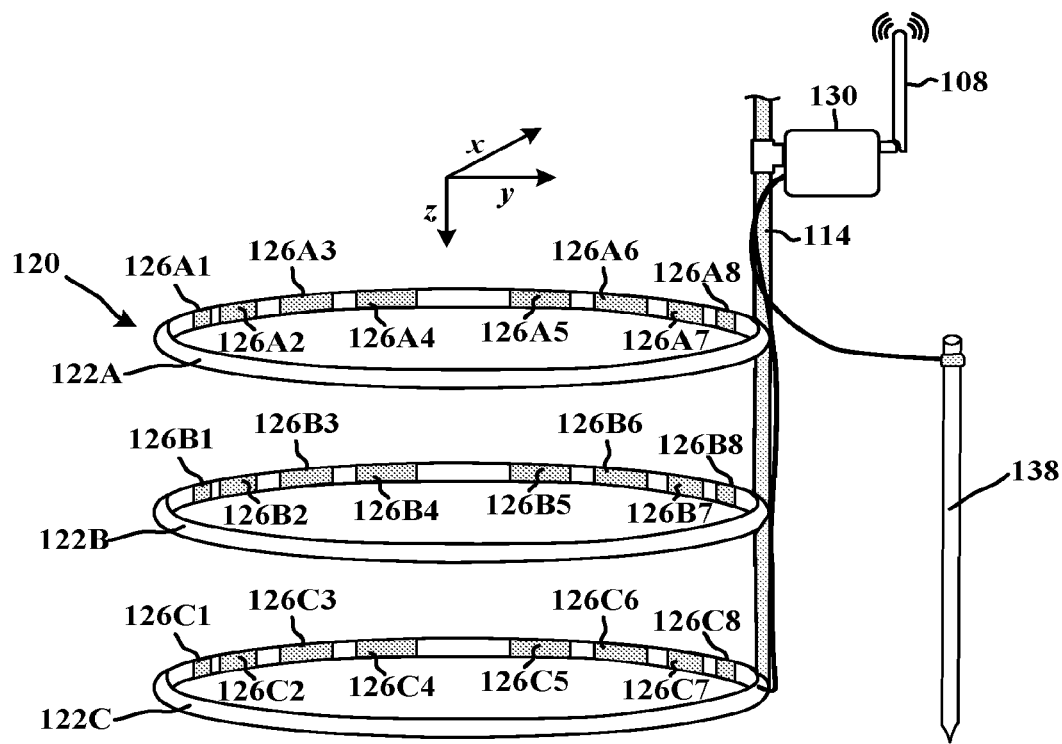

FIGS. 2A and 2B are diagrams illustrating a top-view and an ISO-view of a non-invasive root phenotyping device 100 with conductor plates 126. As depicted in FIG. 2B, the circular supports 122A, 122B, 122C are arranged parallel to and separated from each other along the z-axis. The circular support 122A corresponds to a top ring of cage structure 120 (e.g., first row), circular supports 122B correspond to a middle ring of cage structure 120 (e.g., first row), and circular support 122C corresponds to a bottom ring of cage structure 120 (e.g., third row). Each circular support 122A, 122B, 122C includes a plurality of conductor plates 126 that are arranged at a fixed spatial location on the x-y plane on or around the surface of the ring. Each root sensor is designated a location with a distinct identifier that is spatially mapped to controller 130. For example, the plurality of conductor plates 126 are designated 126A1-126A8, 126B1-126B8, 126C1-126C8 etc., where the "A," "B," and "C" corresponds to rows and the "1"-"8" corresponds to columns. The physical location for each designated electronic sensor 126A1-126A8, 126B1-126B8, 126C1-126C8 can easily be determined and spatially mapped to the controller 130.

In some examples, one or more of the supports (e.g., vertical supports 110 and extended vertical support 114) are removable (e.g., vertical support 114). As depicted in FIG. 2B, supports 110 have been removed. In some examples, extendible vertical support 114 is a removable and/or extendible rod that slides into the cage structure 120. In such an instance, the extendible vertical support 114 elements affixed thereto can be removed from the soil and the rest of root phenotyping device 100. Further, the removable aspect facilitates microcontroller 130, solar panel 132, soil sensor 134, and ambient sensor 136 to be removed (e.g., at the end of a growing season). It should be appreciated that each component, once removed, can be reused for another plant or growing season.

It should be appreciated that the support structure can be constructed to accommodate other spatially viable positions for conductor plates 126. For example, in some instances the support structure can be a tapered such that the column positions of the conductor plates 126 in an adjacent ring are vertically skewed (e.g., positioned in a different x, y, and z position). In some instances, the support structure can contour to the surface of a sphere, cone, cylinder, etc.

Figure 3A:
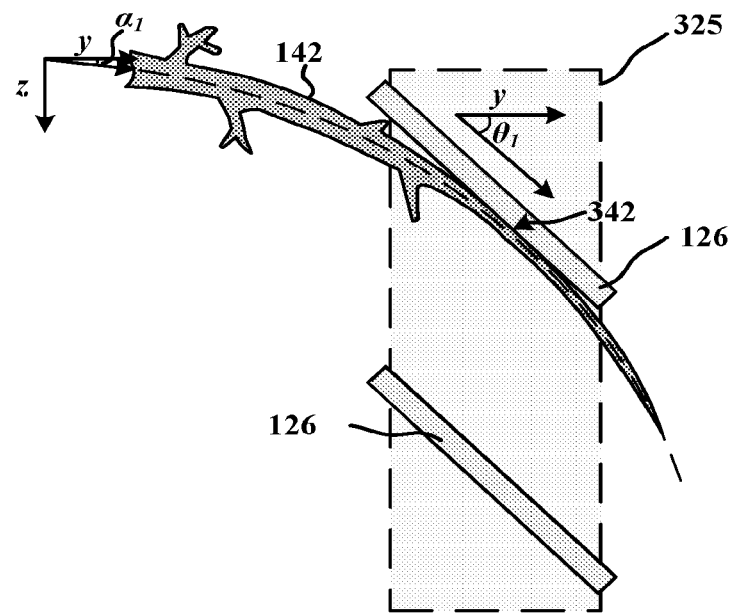
FIGS. 3A and 3B are diagrams illustrating an example of cross-sections of conductor plates tilted at oblique angle with respect to the base of a root.
Figure 3B:
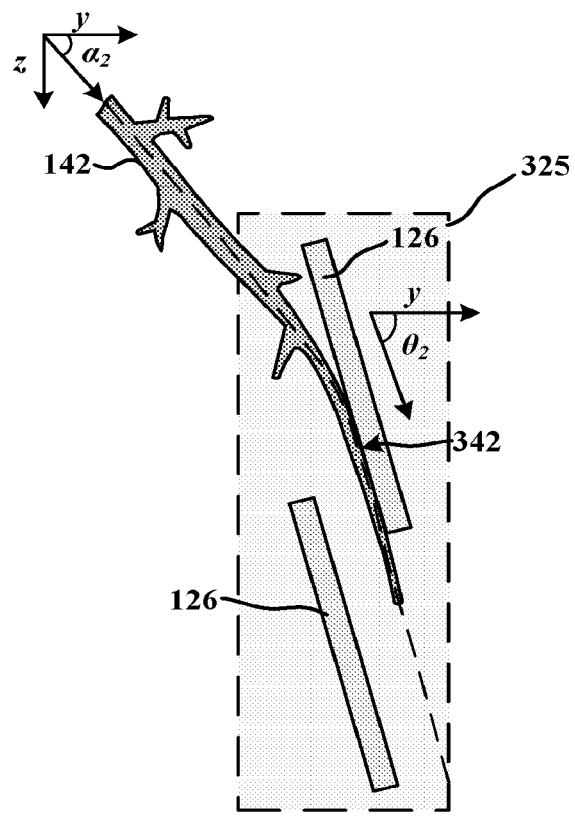

FIGS. 3A and 3B are diagrams illustrating an example of cross-sections of conductor plates 126 tilted at oblique angles with respect to the base of a root 142. The root sensor is situated at a slant from the +y direction (e.g., y axis) toward the +z direction (e.g., z axis) with respect to a lateral (x-y plane) base of the root 142. This configuration is less invasive to the plant 140, as the roots 142 are naturally angled with respect to the base of the root 142. Conceptually, the oblique angle (e.g., $\theta_1$, $\theta_2$) is slight angled downward (e.g., toward the z-axis) from the root angle (e.g., $\alpha_1$, $\alpha_2$). This provides for a greater surface area along the point of contact 342 with the conductor plates 126. For example, the root 142 depicted in FIG. 3A has shallow roots with a root angle $\alpha_1$ from the lateral direction (e.g., y axis), and the conductor plate 126 is situated at an angle of $\theta_1$, which is greater than the root angle $\alpha_1$. This configuration reduces the obstruction area of the root 142 while providing a greater surface area for the root to grow along the surface 342 of the conductor plate 126. Likewise, the root 142 depicted in FIG. 3B has shallow roots with a root angle $\alpha_2$ from the lateral direction (e.g., y axis), and the conductor plate 126 is situated at an angle of $\theta_2$, which is greater than the root angle $\alpha_2$.

In general, the root angle $\alpha_2$ depicted in FIG. 3B is for deep roots that are situated below the shallow roots with a root angle $\alpha_1$ depicted in FIG. 3A. As such, the support structure (e.g., cage structure 120) of phenotyping device 100 can affix the plurality of conductor plates 126 at various oblique angles. In some examples, the oblique angles of the conductor plate 126 vary with depth (e.g., z-axis). In some examples, the oblique angles of conductor plate 126 near the surface are less than or equal to the oblique angles of conductor plate 126 situated vertically lower. In some examples, the oblique angles of conductor plate 126 near the surface are greater than the oblique angles of conductor plate 126 situated vertically lower.

As depicted in FIGS. 3A and 3B the plurality of conductor plates 126 are affixed to support structure 325. The support structure can be positioned between the vertical supports 110 (or the extended vertical support 114) and the lateral supports (e.g., circular supports 122A, 122B, 122C). The support structure can be made from biodegradable and/or compostable material such as cotton, bamboo, soy protein fabric, wool, tencel, wood, polylactic acid (PLA), poly-3-hydroxybutyrate (PHB), polyhydroxyalkanoates (PHA), and the like. The support structure can be made from a non-reactive metal (e.g., stainless steel) or a highly conductive metal (e.g., copper, galvanized steel, etc.). It should be appreciated that conductor plates 126 are electrically insulated from the non-reactive metal or highly conductive metal. In some examples, the support structure 325 is mesh that can be made from twines (e.g., cords, threads, or wire) surrounding open spaces. The open spaces provide a path for the roots 142 to grow without obstruction.

Figure 4A:
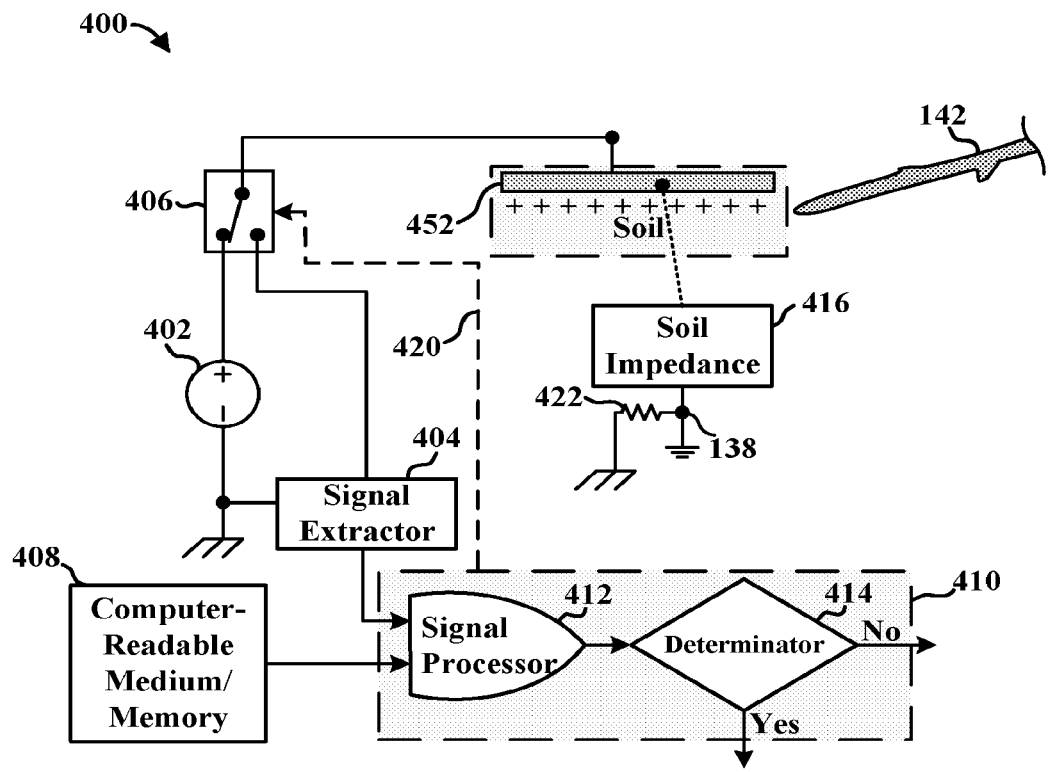
FIGS. 4A and 4B are circuit diagrams illustrating an example of a root contact sensor configured to determine whether a root is in contact with the root conductor plate.
Figure 4B:
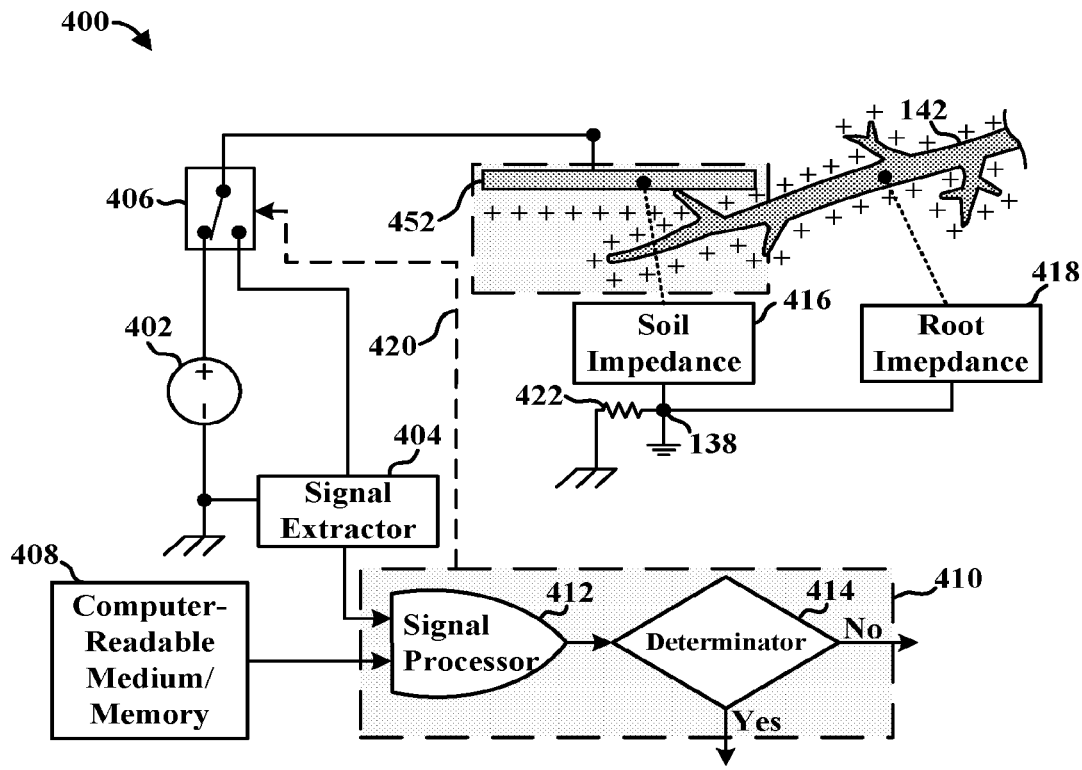

FIGS. 4A and 4B are circuit diagrams illustrating an example of a root contact sensor 400 configured to determine whether a root 142 is in contact with the root conductor plate 126. The root contact sensor 400 includes a switch 406 electrically coupled to a first conductor plate 452, a power supply 402, a signal extractor 404, and a microprocessor 410. The first conductor plate 452 is an electrically conductive plate situated in the soil. The first conductor plate 452 can be made from a non-reactive metal (e.g., stainless steel) or a highly conductive metal (e.g., copper, galvanized steel, etc.). As depicted in FIG. 1, an electrode 138 is inserted into the soil to provide a good electrical coupling to earth ground. As such, the soil impedance 416 provides a conduit for charges to flow from the first conductor plate 452 through the soil to an electrode 138. Charge applied to the first conductor plate 452 can build up or dissipate depending on the electrical properties (e.g., impedance 416) of the soil. For example, for wet salty soils the impedance can be low (e.g., resistivity ~10 $\Omega$-m), and for dry soils the impedance can be high (e.g., resistivity ~1 k$\Omega$-m). Likewise, for very dry soils the impedance can be even higher (e.g., resistivity ranging between 1 k$\Omega$-m to 10 k$\Omega$-m).

It should be appreciated that earth ground and chassis ground can have different voltage potentials (e.g., $V_{Earth} \neq V_{Chassis}$). That is, even for instances where an electrical wire shorts the chassis ground to earth ground, the electrical wire connection has a non-zero line impedance 422. In some instances of poor grounding, the electrode 138 can be positioned on the chassis ground rather than the earth ground depicted in FIGS. 4A and 4B.

The switch 406 is configured to switch between a first mode and a second mode. In the first mode, the power supply 402 is enabled to provide an electrical charge to the first conductor plate 452. As depicted in FIG. 4A, the power supply 402 is electrically coupled to the first conductor plate 452. In this configuration, a charge (e.g., voltage potential) builds up due to the non-zero impedance (e.g. resistivity) between the first conductor plate 452 and the electrode 138. In the second mode, the signal extractor 404 is enabled to capture the signal response. In this configuration, the power supply 402 is electrically uncoupled from the first conductor plate 452, and the signal extractor 404 is electrically coupled to the first conductor plate 452. In turn, the charge dissipates over time as electrons flow from the earth ground of the electrode 138 through the soil to the first conductor plate 452.

In some examples, the switch 406 can be a multiplexor that is electrically coupled to and controlled by the microcontroller 410. A multiplexer facilitates electrical coupling to a plurality of conductor plates 126 to share outputs (e.g., electrical coupling to power supply 402 and signal extractor 402). For example, microcontroller 410 of the root phenotyping device 100 can include control lines 420 to control the switching of a multiplexor (e.g., switch 406) that electrically couples a plurality of conductor plates 126 to a single power supply 402 or that electrically couples a plurality of conductor plates 126 to a single signal extractor 404. In some examples, the switch 406 is a relay that is electrically coupled to and controlled by the microcontroller 410.

The signal extractor 404 is configured to extract (e.g., capture) a signal response at the first conductor plate 452. In the second mode of the switch 406, the signal extractor 404 captures the voltage at the first conductor plate 452 over time as the charge dissipates, which yields a signal response proportional to electrical properties of the soil (e.g., soil impedance 416). In some examples, the signal extractor is a voltage divider, where the extracted voltage is a ratio of impedances (e.g., $v_0=Z_1/(Z_1+Z_2) \times v_{in}$). In some examples, signal extractor 404 is an analog-to-digital converter (ADC) configured to convert the signal response to digital equivalents. In such an example, the ADC can be configured to digitally capture the signal response. It should be appreciated that the extracted signal (e.g., voltage) from the ADC is with respect to the chassis ground of controller 130, which is common to a plurality of conductor plates 126.

In some examples, signal extractor 404 can be configured to store the extracted signal response in computer readable medium/memory 408 at predetermined (e.g., periodic) intervals. For example, in some instances the signal extractor 404 can store a signal response every five minutes that can be aggregated or retrieved for further processing.

The root contact sensor 400 can further include a microcontroller 410 configured to receive a raw response signal from the signal extractor 404. As depicted in FIG. 4A, the microcontroller 410 includes a signal processor 412 that receives and conditions the raw response signal suitable for comparison. For example, the raw response signal can have high-frequency noise and the signal processor 412 can apply a low-pass filter (e.g., Butterworth filter, Chebyshev filter, Cauer filter, etc.) to condition the signal response.

Signal processor 412 is also configured to retrieve a baseline signal response from computer readable medium/memory 408 and compare portions of the signal response to portions of the baseline signal response. A baseline signal response is a signal response of the root contact sensor 400 under conditions similar to the conditions at the site of the plant. For example, in one instance, the soil sensor 134 can detect the resistivity of the soil at a designated temperature. In turn, the signal processor 412 can retrieve from the computer readable medium/memory 408 (e.g., query a database) a baseline response signal for a soil that has similar resistivity and temperature to compare with the conditioned signal response. It should be appreciated that additional soil characteristics can also be applied when determining a baseline response signal such as salinity, aeration, etc. In some examples, the soil sensor 134 is a soil humidity sensor or a temperature sensor electrically coupled to the microcontroller 410. In some examples, the ambient sensor 136 is a humidity sensor or a temperature sensor electrically coupled to the microcontroller 410.

In some examples, the baseline response signal is determined from aggregated response signals from the conductor plates 126. For example, in the early stages of plant growth (e.g., prior to root development), signal response samples can be stored and aggregated based on the soil characteristics. In general, the baseline signal response is representative of a signal response of the conductor plate 126 in soil without a root 142 that is in contact with the first conductor plate 452 under similar conditions (e.g., salinity, resistivity, temperature, aeration, etc.).

The microcontroller 410 includes a determinator 414 that compares the conditioned signal response to the baseline signal response to determine whether a root 142 is present. As depicted in FIG. 4A, root 142 is in proximity to the first conductor plate 452, but it does not physically contact conductor plate 354. As such, the charge on the first conductor plate 452 is not distributed on the root 142, which provides additional electrical paths (e.g., root impedance 418) for dissipation. Instead, the charge is confined to the first conductor plate 452 for dissipation through the soil (e.g., soil impedance) to the first conductor plate 452. The dissipation of the charge has a characteristic signal response profile that is sufficiently similar to a baseline signal response.

The determinator 414 compares the conditioned signal to the baseline signal. In the example depicted in FIG. 4A, the determinator 414 determines that no root 142 is detected because the conditioned response signal is sufficiently similar to the baseline signal response (e.g., signal response without a root present). In some examples, determinator 414 is a digital comparator configured to determine whether the difference between portions of the conditioned signal response and portions of the baseline signal response exceeds a threshold value. In one instance, a portion of the baseline signal response can be a peak (e.g., max or relative max value) that corresponds to a peak (e.g., max or relative max value) of the conditioned signal response. In such an instance, the determinator 414 can determine that no root is detected for a peak of the conditioned signal response that exceeds a threshold value (e.g., 90% of peak from baseline signal).

As depicted in FIG. 4B, root 142 is in physical contact with the first conductor plate 452. As such, the charge on the first conductor plate 452 is distributed throughout root 142. The distribution of charge provides an additional electrical path (e.g., root impedance 418) for dissipation. In this example, the charge is no longer confined to the first conductor plate 452 for dissipation through the soil (e.g., soil impedance 416 path). Instead, the charge is distributed along the root 142 (e.g., root impedance 416 path), which changes the characteristic signal response profile from the baseline signal response.

The determinator 414 compares the conditioned signal to the baseline signal, and the determinator 414 determines that electrical perturbations from the root 142 in physical contact with the first conductor plate 452 produce a response signal dissimilar to the baseline signal response (e.g., signal response without a root present). In some examples, determinator 414 is a digital comparator configured to determine whether the difference between portions of the conditioned signal response and portions of the baseline signal response does not exceed a threshold value. For instance, the determinator 414 can determine that a root is detected when a peak of the response signal does not exceed a threshold value (e.g., 90% of peak from baseline signal). That is, a root presence is associated with a determination that the signal response exceeded the threshold value. It should be appreciated that a baseline signal response can include a signal response of a root in physical contact with the first conductor plate 452. In such an instance, the determinator 414 can determine that a root is detected when the response signal is similar to the baseline signal.

As depicted in FIGS. 4A and 4B, the root contact sensor 400 can further include a computer readable medium/memory 408 electrically coupled to the microcontroller 410. The computer readable medium/memory 408 is configured to store data associated with the signal extractor. In some examples, the computer readable medium/memory 408 is RAM, ROM, EEPROM, and the like. The computer readable medium/memory 408 can include a database of baseline signal responses for various soil conditions at the site of the plant such as resistivity, salinity, moisture content, temperature, aeration, aggregation (e.g., rocky, clay, sand), and the like.

Figure 5C:
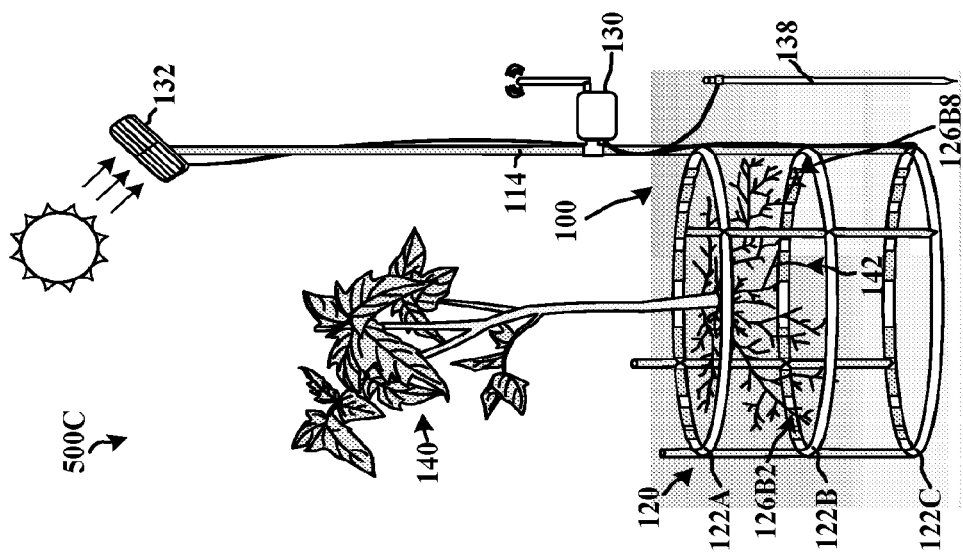
FIGS. 5A-5C are diagrams illustrating an example of a non-invasive root phenotyping device with a plurality of conductor plates surrounding a plant at various stages of growth of a plant root system over time.
Figure 5B:
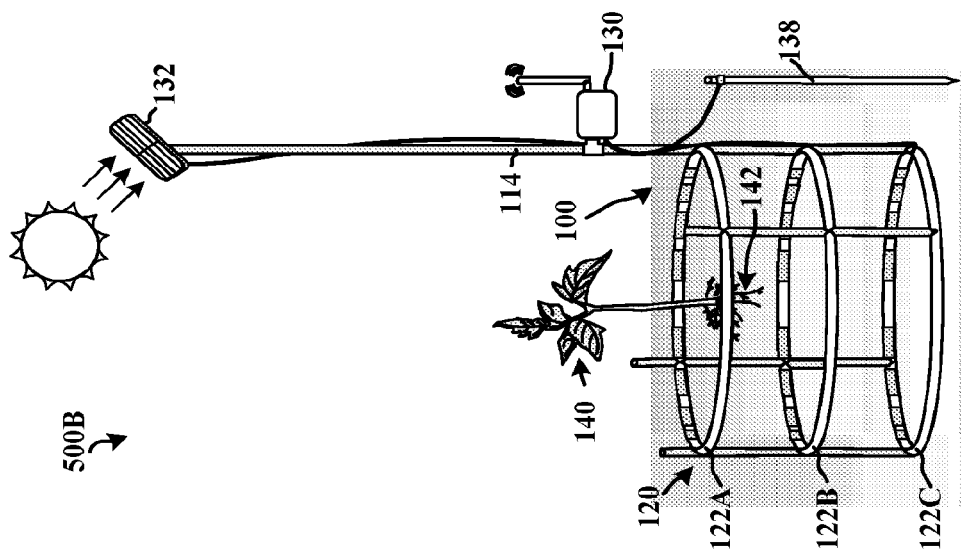
Figure 5A:
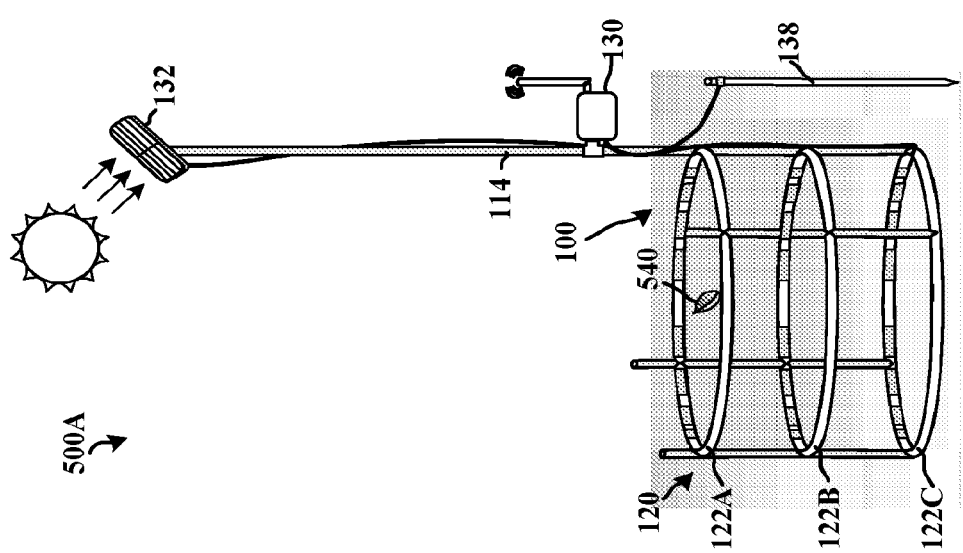

FIGS. 5A-5C are diagrams illustrating an example of a non-invasive root phenotyping device 100 with a plurality of conductor plates 126 surround a plant at various stages of growth of a plant root system over time 500A, 500B, 500C. As depicted in FIGS. 5A-5C, the root phenotyping device 100 includes a plurality of conductor plates 126 affixed (e.g., trellised) to cage structure 120 and are similar to the root phenotyping device 100 depicted in FIG. 1. At time 500A, seed 540 is planted in a soil at a specified location at a known depth. The root phenotyping device 100 is buried around soil location such that the location of seed 540 is at or near an approximate center of cage structure 120. In some examples, the root phenotyping device 100 can be buried prior to time 500A depicted in FIG. 5A. For example, multiple root phenotyping devices 100 can be installed along a row at an instance in time, and individual seeds 540 can be planted at or near the center of each root phenotyping device 100 at a later instance in time using an automated planter. In some instances, root phenotyping device 100 can be buried after seed 540 has been planted without interfering with the roots 142. For example, the root phenotyping device 100 can be buried while plant 140 is at a stage in growth similar to that depicted in FIG. 5B.

FIG. 5B represents a later time than FIG. 5A, where the seed 540 has sprouted and has grown into a small plant with relatively small roots 142 that emanate from the known planted location. In this instance, the roots 142 emanate from the plant 140 at the origin of where the seed 540 had been planted in FIG. 5A. As depicted in FIG. 5B, the root phenotyping device 100 does not detect a root 142 in contact with a first conductor plate 452 because the roots do not touch the conductor plate 126.

FIG. 5C represents a later time than FIG. 5B, where the plant 140 and the roots 142 have grown. In this instance, the roots 142 have grown sufficiently to contact various conductor plates 126 affixed to the top circular structure 122A and the middle circular structure 122B. In this instance, the conductor plate 126B2 and conductor plate 126B8 are in physical contact with a root 142. In turn, the extracted signal response is conditioned and compared to a baseline signal response, and it is determined by the microcontroller 410 that a root 142 is in contact with a first conductor plate 452 at a location associated with conductor plate 126B2 and conductor plate 126B8 at a designated time (e.g., timestamp).

In some instances, the conductor plates 126 have not detected a root 142 below row 126B (e.g., no root at 126C, 126D, etc.). In such an instance, the root phenotyping devices 100 can determine the root approximate growth rate (e.g., distance to conductor plate 126B2, 126B8 divided by the time of initial detection) as well as the approximate depth of the root system.

Figure 6A:
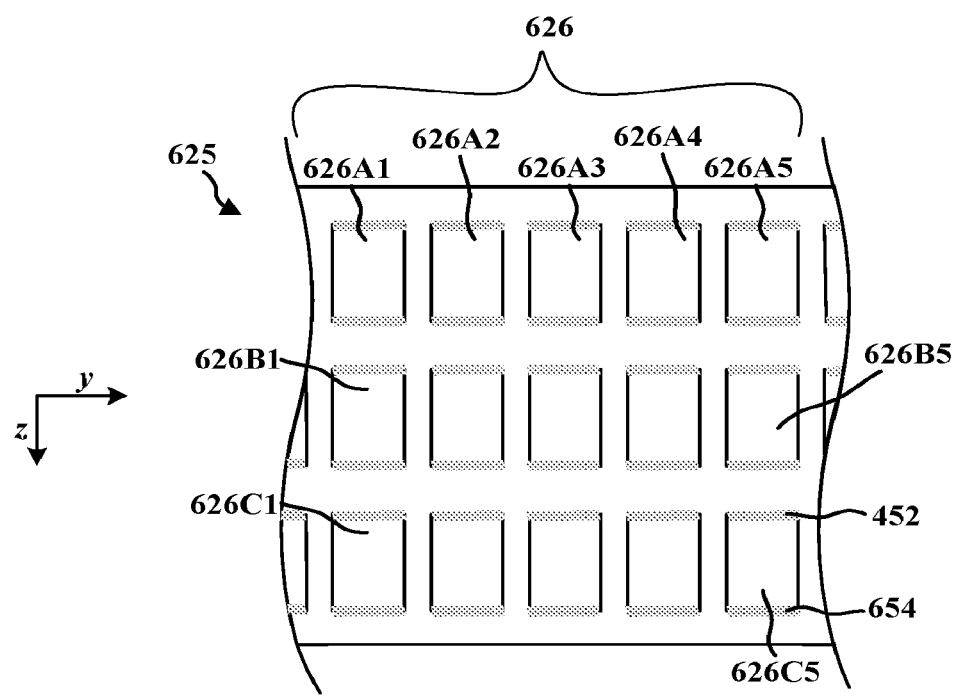
FIG. 6A is a diagram illustrating a side-view of a portion of a sensor array for a non-invasive root phenotyping device with a plurality of parallel conductor plates.

FIG. 6A is a diagram illustrating a side-view of a portion of a sensor array 625 for a non-invasive root phenotyping device with a plurality of parallel conductor plates 626. In this example, each parallel conductor plate 626 is designated a spatial location with a distinct identifier that is mapped to controller 130. The plurality of parallel conductor plates 626 are designated 626A1-626A5, 626B1-626B5, 626C1-626C5 etc., where the "A," "B," and "C," correspond to rows and the "1"-"5" correspond to columns. From this mapping the controller 130 can spatially map a detected root 142.

It should be appreciated that the support structure can be constructed to accommodate other spatially viable positions for the parallel conductor plates 626. For example, in some instances the support structure can be tapered such that the column positions of the parallel conductor plates 626 in an adjacent circular structure are vertically skewed (e.g., positioned in a different x, y, and z position). In some instances, the support structure along with trellised sensor array 625 can contour to a spherical shape, conical shape, cylindrical shape, etc.

As depicted in FIG. 6A, a parallel conductor plate 626 includes a first conductor plate 452 adjacent to and substantially parallel to a second conductor plate 654. The region between the first conductor plate 452 and the second conductor plate 654 is filled with soil. As discussed supra, the impedance between the first conductor plate 452 and the second conductor plate 654 can vary based on the electrical properties (e.g., impedance 416) of the soil, such as soil type (e.g., clay, sand, aggregate, etc.), moisture content, and nutrients (e.g., phosphate, nitrate, potassium, salts, etc.). As depicted in FIG. 6A, the first conductor plate 452 and the second conductor plate 654 for each parallel conductor plates 626 are oriented laterally (e.g., along the y-axis). In some examples, the first conductor plate 452 and/or the second conductor plate 654 for one or more electronic sensors can be tilted at oblique angles with respect to the base of a root 142, as depicted in FIGS. 2A and 2B. In some examples, the first conductor plate 452 and the second conductor plate 654 for one or more electronic sensors can be positioned sidelong (e.g., along the z-axis).

It should be appreciated that the gap between the first conductor plate 452 and the second conductor plate 654 can vary in distance and cross sectional area. In some examples, a gap between the first conductor plate 452 and the second conductor plate 654 has a cross sectional area of less than or equal to about 1 cm$^2$. In some examples, a distance between the first conductor plate 452 and the second conductor plate 654 is equal to or greater than about 1 mm.

Figure 6B:
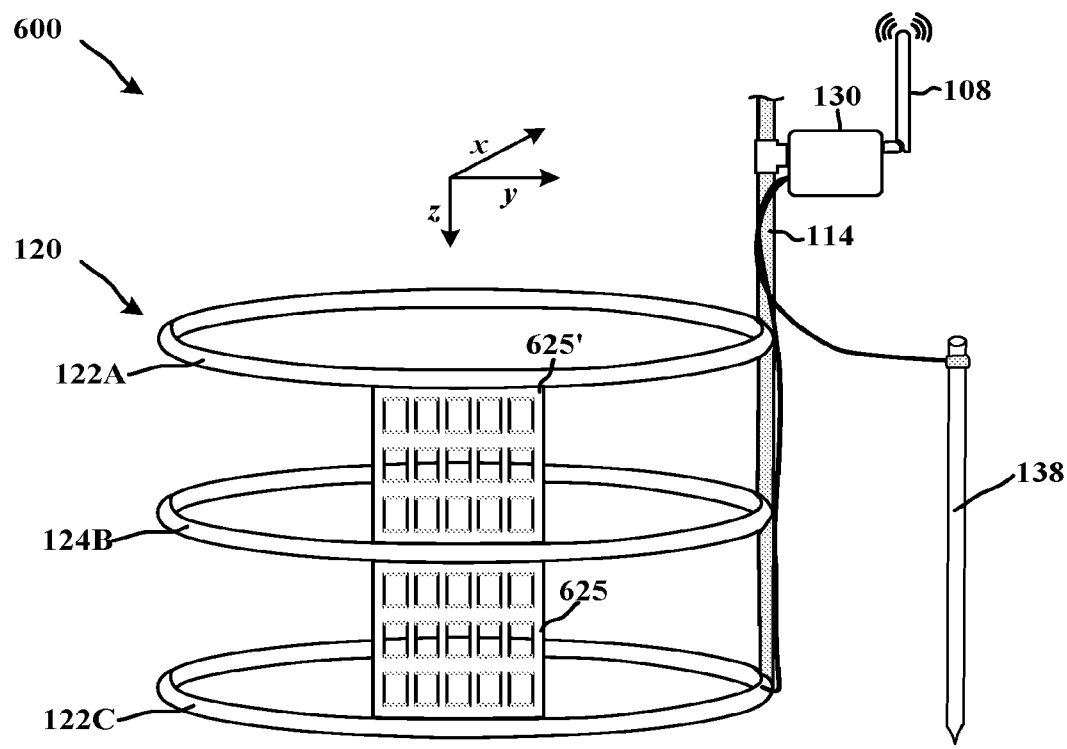
FIG. 6B is a diagram illustrating an ISO-view of a non-invasive root phenotyping device with a portion of sensor array and a plurality of parallel conductor plates trellised between circular supports.

FIG. 6B is a diagram illustrating an ISO-view of a non-invasive root phenotyping device 600 with a portion of sensor array 625 with a plurality of parallel conductor plates 626 trellised between circular supports 122A, 122B, 122C. In this example, the support structure is a cage structure 120 with top circular support 122A (e.g., first row), middle circular support 122B (e.g., second row), and bottom circular supports 122C (e.g., third row) vertically (e.g., along the z-axis) connected to extended vertical support 114, which forms a backbone for the support structure. The circular supports 122A, 122B, 122C are arranged parallel and separate from each other along the z-axis. Although not depicted, the root phenotyping device 600 can include vertical supports 110 for additional support.

As depicted in FIG. 6B, a portion of sensor array 625 is situated between the bottom circular support 122C and the middle circular support 122B. Likewise, a duplicate of the portion of sensor array 625' is situated between top circular support 122A and the middle circular support 122B. In some examples, a portion of sensor array 625, is extended around the circular supports 122A, 122B, 122C to enclose a cylindrical surface around the plant 140. In some examples, a portion of sensor array 625 is affixed to the circular section of the bottom circular support 122C to enclose a bottom circular portion of the cylindrical section. In some examples, additional sensor arrays 625 are attached to one or more second circular supports outside the circular supports 122A, 122B, 122C.

As in the example depicted in FIG. 1, the cage structure 120 of non-invasive root phenotyping device 600 is made from any material that resists deformation upon insertion into a desired soil type without affecting the health and growth of the plant 140. For example, the cage structure 120 material is made from metal (e.g., galvanized steel, stainless steel), plastic (e.g., bioplastics), and the like. In some examples, the cage structure 120 is made from biodegradable and/or compostable material such as polylactic acid (PLA), poly-3-hydroxybutyrate (PHB), polyhydroxyalkanoates (PHA), and the like. In some instances, a 3-D printer can be utilized to construct the cage structure 120 using a suitable thermoplastic (e.g., PLA, etc.). In some instances, the cage structure 120 can be injected molded using a suitable thermoplastic (e.g., PLA, etc.).

Although vertical supports 110 are not depicted in FIG. 6A, it should be appreciated that, in some examples, the vertical supports 110 can be affixed to the circular supports 122A, 122B, 122C to provide additional strength and rigidity to the non-invasive root phenotyping device 600 Likewise, other components depicted in the non-invasive root phenotyping device 100 of FIG. 1 can be implemented in root phenotyping device 600. For example, it should be appreciated that examples of the non-invasive root phenotyping device 600 can include a solar cell 132, soil sensor 134, ambient sensor 136, and the like.

Figure 7A:
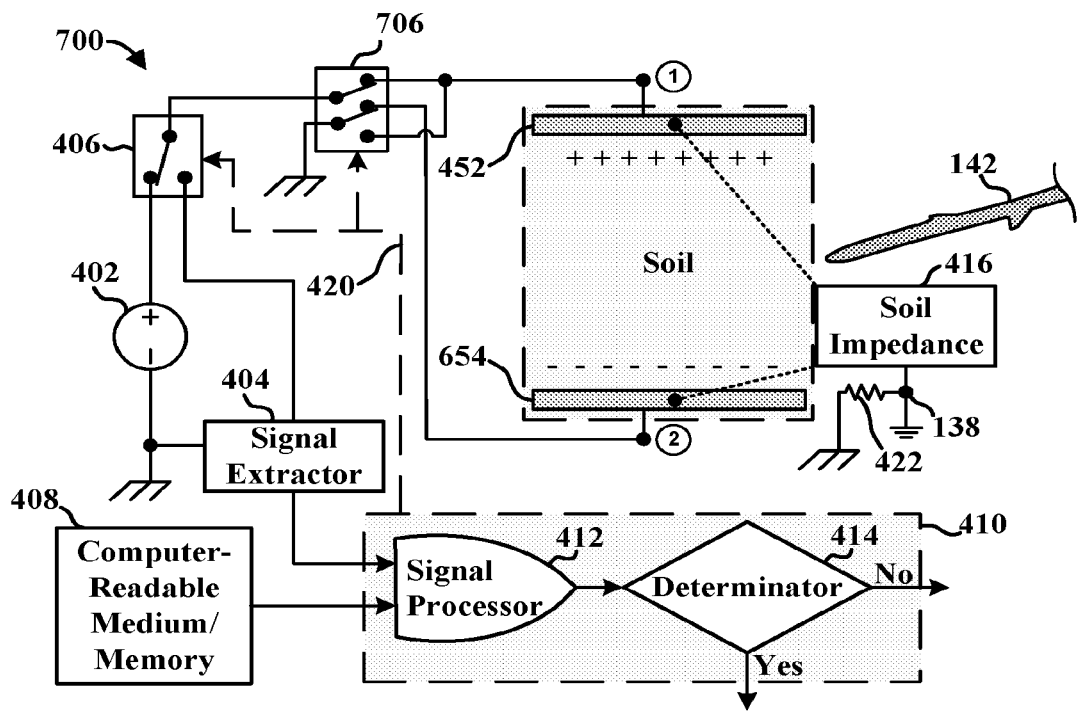
FIGS. 7A and 7B are circuit diagrams illustrating an example of a root proximity sensor in an instance where a root is absent from between first conductive plate and the second conductor plate.
Figure 7B:
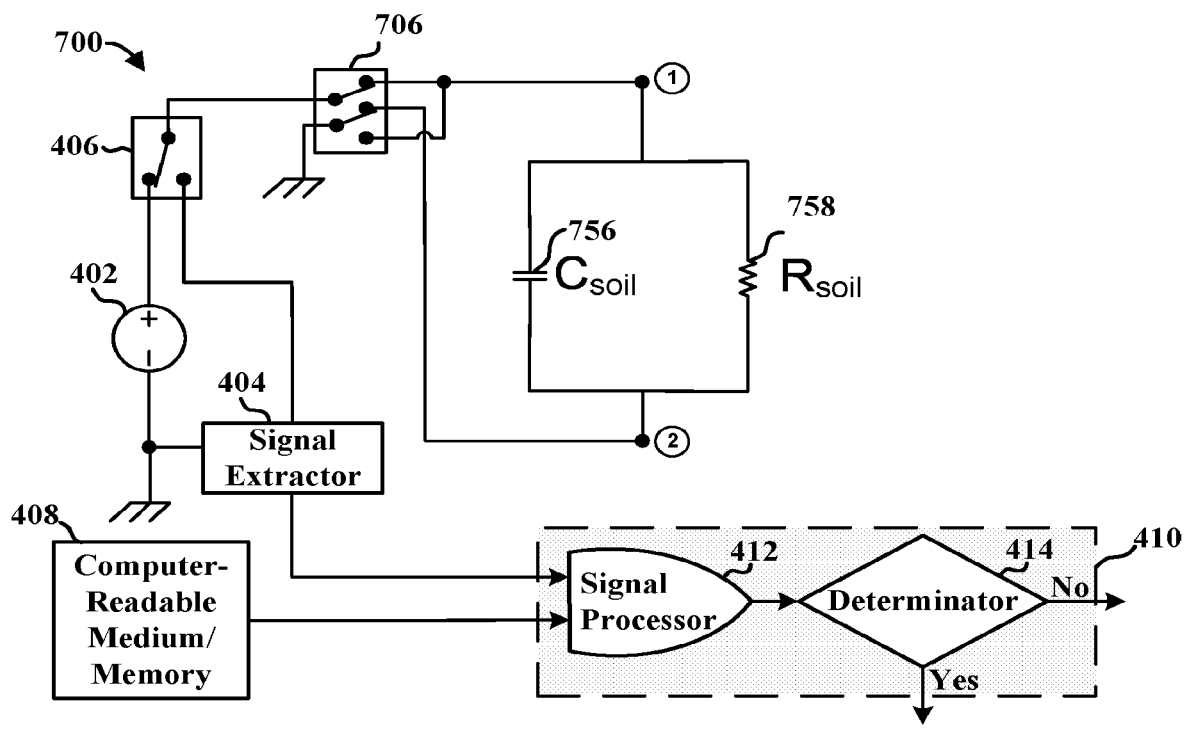

FIGS. 7A and 7B are circuit diagrams illustrating an example of a root proximity sensor 700 in an instance where a root 142 is absent from between a first conductive plate 452 and a second conductor plate 654. The root proximity sensor 700 includes a first conductor plate 452 and a second conductor plate electrically coupled to ground (e.g., chassis ground). The second conductor plate 654 is adjacent to the first conductor plate 452 and substantially parallel to the first conductor plate 452. The first conductor plate 452 and the second conductor plate are electrically conductive plates situated in the soil, as depicted in FIG. 7A. The first conductor plate 452 and the second conductor plate 654 can be made from a non-reactive metal (e.g., stainless steel) or a highly conductive metal (e.g., copper, galvanized steel, etc.). In this example, an electrode 138 is inserted into the soil to provide a good electrical coupling to earth ground, as depicted in FIG. 1. As such, the soil impedance 416 provides a conduit for charges to flow from the conductor plate 654 through the soil to an electrode 138. Charge applied to the first conductor plate 452 can build up or dissipate depending on the electrical properties (e.g., impedance 416) of the soil.

It should be appreciated that earth ground and chassis ground can have different voltage potentials (e.g., $V_{Earth} \neq V_{Chassis}$). That is, even for instances where an electrical wire shorts the chassis ground to earth ground, the electrical wire connection has a non-zero line impedance 422. In some instances of poor grounding, the electrode 138 can be positioned on the chassis ground rather than the earth ground depicted in FIG. 7A.

The root proximity sensor 700 further includes a switch 406 electrically coupled to the first conductor plate 452, a power supply 402, a signal extractor 404, and a microprocessor 410. The switch 406 is configured to switch between a first mode and a second mode. In the first, mode the power supply 402 is enabled to provide an electrical charge to the first conductor plate 452. As depicted in FIG. 7A, the power supply 402 is electrically coupled to the first conductor plate 452, and, as such, a slight charge (e.g., voltage potential) will build up due to the non-zero soil impedance 416 (e.g., resistivity) between the first conductor plate 452 and the second conductor plate 454, as well as the soil impedance 416 (e.g., resistivity) between the first conductor plate 452 and the electrode 138.

In the second mode, the signal extractor 404 is enabled to capture the signal response. In this configuration, power supply 402 is electrically uncoupled from the first conductor plate 452, and the signal extractor 404 is electrically coupled to the first conductor plate 452. As such, the charge dissipates over time as electrons flow in the soil across the gap between the second conductor plate 654 and the first conductor plate 452, as well as from the earth ground of the electrode 138 through the soil to the conductor plate 654.

In some examples, the switch 406 can be a multiplexor that is electrically coupled to and controlled by the microcontroller 410. A multiplexer facilitates electrical coupling to a plurality of parallel conductor plates 626 (shown in FIGS. 6A and 6B) to shared terminals (e.g., electrical coupling to power supply 402 and electrical coupling to signal extractor 402). For example, microcontroller 410 of the root phenotyping device 100 can include control lines 420 to control the switching of a multiplexor (e.g., switch 406) that electrically couples a plurality of parallel conductor plates 626 to a single power supply 402 or that electrically couples a plurality of parallel conductor plates 626 to a single signal extractor 404. In some examples, the switch 406 is a relay that is electrically coupled to and controlled by (e.g., via control lines 420) the microcontroller 410.

The signal extractor 404 is configured to capture a signal response at the first conductor plate 452. In the second mode of the switch 406, the signal extractor 404 captures the voltage at the first conductor plate 452 at instances in time as the charge dissipates, which yields a transient signal response proportional to electrical properties of the soil (e.g., soil impedance 416). In some examples, the signal extractor is a voltage divider, where the extracted voltage is a ratio of impedances (e.g., $v_o = Z_1/(Z_1+Z_2) \times v_{in}$). In some examples, signal extractor 404 is an ADC configured to convert the signal response to digital equivalents. In such an example, the ADC can be configured to digitally capture the signal response. It should be appreciated that the signal (e.g., voltage) from the ADC is extracted with respect to the chassis ground of controller 130, which is common to a plurality of parallel conductor plates 626.

In some examples, signal extractor 404 can be configured to store the extracted signal response in computer readable medium/memory 408 at predetermined (e.g., periodic) intervals. For example, in some instances the signal extractor 404 can store a signal response every five minutes that can be aggregated or retrieved for further processing.

The root proximity sensor 700 can further include a microcontroller 410 configured to receive a raw response signal from the signal extractor 404. As depicted in FIG. 7A, the microcontroller 410 includes a signal processor 412 that receives and conditions a response signal suitable for comparison. For example, the raw response signal can have high-frequency noise. In such an instance, the signal processor 412 can apply a low-pass filter (e.g., Butterworth filter, Chebyshev filter, Cauer filter, etc.) to condition the signal response.

Signal processor 412 is also configured to retrieve one or more baseline signal responses from computer readable medium/memory 408 and compare portions of the signal response to portions of the baseline signal response. A baseline signal response is a signal response of the root proximity sensor 700 under conditions similar to the conditions at the site of the plant. For example, in one instance, the soil sensor 134 can detect the resistivity of the soil at a designated temperature. In turn, the signal processor 412 can retrieve from the computer readable medium/memory 408 (e.g., query a database), a baseline response signal for a soil that has similar resistivity and temperature to compare with the conditioned signal response. It should be appreciated that additional soil characteristics can also be applied when determining a baseline response signal such as salinity, aeration, etc. In some examples, the soil sensor 134 is a soil humidity sensor or a temperature sensor electrically coupled to the microcontroller 410. In some examples, the ambient sensor 136 is a humidity sensor or a temperature sensor electrically coupled to the microcontroller 410.

In some examples, the baseline response signal is determined from aggregated response signals extracted from the plurality of parallel conductor plates 626. For example, in the early stages of plant growth (e.g., prior to root elongation), signal response samples can be stored and aggregated based on the soil characteristics. In general, the baseline signal response is representative of a signal response of the parallel conductor plate 626 in soil without a root 142 between the first conductor plate 452 and the second conductor plate 654 under similar conditions (e.g., salinity, resistivity, temperature, aeration, etc.).

The microcontroller 410 includes a determinator 414 that compares the conditioned signal response to the baseline signal response to determine whether a root 142 is present. As depicted in FIG. 7A, root 142 is in proximity to the first conductor plate 452 and the first conductor plate 452 but is not in between the first conductor plate 452 and the second conductor plate 654. In this instance, the root 142 is not polarized with electrons attracted to the charged first conductor plate 452 on one side of the root 142 and electrons repelled from the charged first conductor plate 452 on the opposite side of the root 142. As such, the impedance of the soil (e.g., permittivity and permeability) remains substantially unchanged from soils without plant roots.

As depicted in FIG. 7A, the charge is confined to the first conductor plate 452 for dissipation through the soil (e.g., soil impedance). Consequently, the overall impedance of the soil between the first conductor plate 452 and the second conductor plate 654 is the capacitance of the soil $C_{soil}$ in parallel with the overall capacitance of the root $C_{root}$, as depicted in FIG. 7B. In such an example, the first conductor plate 452 will have a characteristic signal response profile that is sufficiently similar to a baseline signal response.

The determinator 414 compares the conditioned signal to the baseline signal. In the example depicted in FIG. 7A, the determinator 414 determines that no root 142 is detected between the first conductor plate 452 and the second conductor plate 654 because the conditioned response signal is sufficiently similar to the baseline signal response (e.g., signal response without a root present). In some examples, determinator 414 is a digital comparator configured to determine whether the difference between portions of the conditioned signal response and portions of the baseline signal response exceeds a threshold value. In one instance, a portion of the baseline signal response can be a peak (e.g., max or relative max value) that corresponds to a peak (e.g., max or relative max value) of the conditioned signal response. In such an instance, the determinator 414 can determine that no root is detected for a peak of the conditioned signal response that exceeds a threshold value (e.g., 90% of peak from baseline signal).

As depicted in FIGS. 7A and 7B, the root proximity sensor 700 can include a polarity switch 706 electrically coupled to switch 406, the first conductor 452 and the second conductor 654. The polarity switch is configured to provide a second configuration that exchanges electrical coupling between the first conductor plate 452 and the second conductor plate 654. That is, the polarity switch 706 reconfigures the electrical coupling such that the first conductor plate 452 is electrically coupled to ground (e.g., chassis ground), and the second conductor plate 654 is electrically coupled to the power supply 402 through the switch 406 in the first mode or the second conductor plate 654 is electrically coupled to signal extractor 404 through the switch 406 in the second mode.

As depicted in FIGS. 7A and 7B, the root proximity sensor 700 can further include a computer readable medium/memory 408 electrically coupled to the microcontroller 410. The computer readable medium/memory 408 is configured to store data associated with the signal extractor. In some examples, the computer readable medium/memory 408 is RAM, ROM, EEPROM, and the like. The computer readable medium/memory 408 can include a database of baseline signal responses for various soil conditions at the site of the plant such as resistivity, salinity, moisture content, temperature, aeration, aggregation (e.g., rocky, clay, sand), and the like.

Figure 8A:
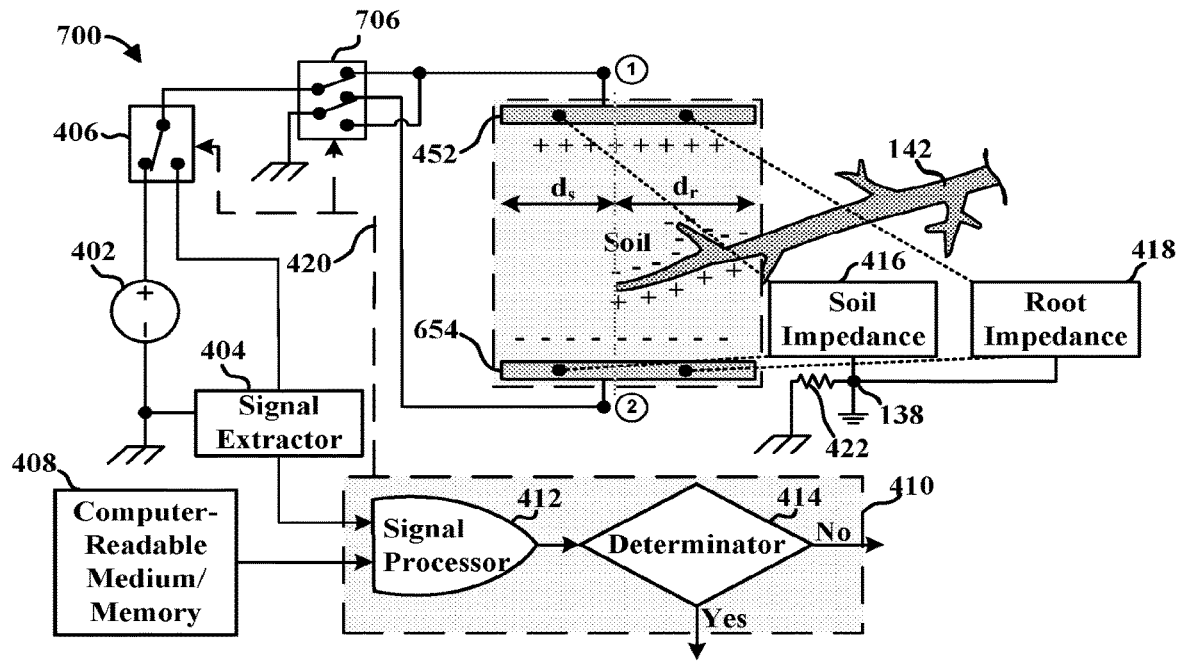
FIGS. 8A and 8B are circuit diagrams illustrating an example of a root proximity sensor in an instance where a root is between the first conductive plate and the second conductor plate.
Figure 8B:
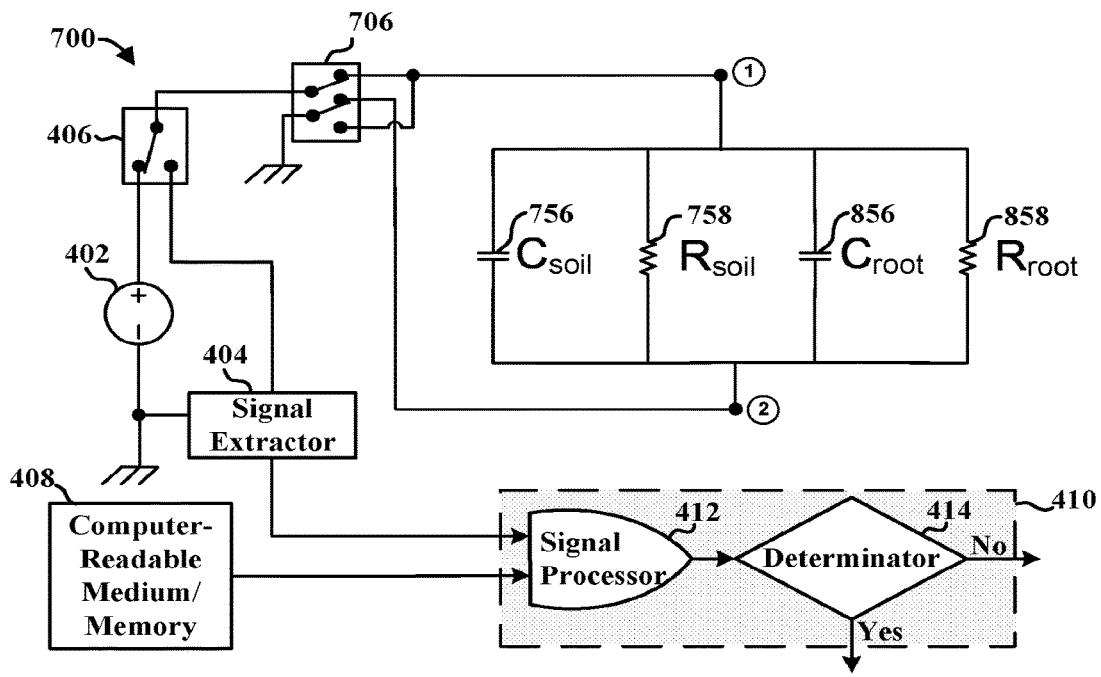

FIGS. 8A and 8B are circuit diagrams illustrating an example of a root proximity sensor 700 in an instance where a root 142 is between the first conductive plate 452 and the second conductor plate 654. The proximity sensor 700 has the same components as described in FIGS. 7A and 7B above. As depicted in FIG. 8A, the root 142 is situated between the first conductor plate 452 and the second conductor plate 654, but it is not in contact with either the first conductor plate 452 or the second conductor plate 654. With the root 142 situated between the first conductor plate 452 and the second conductor plate 654, the root 142 becomes polarized with electrons attracted to the positively charged first conductor plate 452 on the side of the root 142 nearest the first conductor plate 452, and electrons are repelled from the negatively charged second conductor plate 654 on the opposite side of the root 142 nearest the second conductor plate 654. In turn, the polarized root 142 changes the overall impedance characteristics. More specifically, the effective impedance characteristics of a portion of the soil between the first conductive plate 452 and the second conductor plate 654 without a root 142 (e.g., between $d_s$) remains unchanged, whereas the effective impedance characteristics of a portion of the soil changes between the first conductive plate 452 and the second conductor plate 654 with a root 142 (e.g., between $d_r$).

In this instance, the portion of the soil between the between the first conductive plate 452 and the second conductor plate 654 with a root 142 (e.g., between $d_r$) provides an alternate path through root impedance 418, which is an effective impedance characterized by the alternate path for the electrons to flow from the second conductor plate 654 to the polarized root 142 and then from the polarized root 142 to the first conductor plate 452. Consequently, the overall impedance of the soil between the first conductor plate 452 and the second conductor plate 654 becomes the capacitance of the soil $C_{soil}$ in parallel with the overall capacitance of the root $C_{root}$ in parallel with the resistance of the soil $R_{soil}$ in parallel with the overall resistance of the root $R_{root}$, as depicted in FIG. 8B. In some examples, the overall impedance decreases between the first conductive plate 452 and the second conductor plate 654.

It should be appreciated that earth ground and chassis ground can have different voltage potentials (e.g., $V_{Earth} \neq V_{chassis}$). That is, even for instances where an electrical wire shorts the chassis ground to earth ground the electrical wire connection has a non-zero line impedance 422. In some instances of poor grounding, the electrode 138 can be positioned on the chassis ground rather than the earth ground depicted in FIG. 8A.

It should also be appreciated that the capacitance of the soil $C_{soil}$, the overall capacitance of the root $C_{root}$, the resistance of the soil $R_{soil}$, and the overall resistance of the root $R_{root}$, can vary based on the resistivity, salinity, moisture content, temperature, aeration, aggregation (e.g., rocky, clay, sand), and the like. Likewise, the values for the capacitance of the soil $C_{soil}$ in parallel with the resistance of the soil $R_{soil}$ between the configuration depicted in FIG. 7A can be different from the values for the capacitance of the soil $C_{soil}$ in parallel with the resistance of the soil $R_{soil}$ in the configuration depicted in FIG. 8A.

Because the charge is no longer confined to the first conductor plate 452 for dissipation through the soil (e.g., soil impedance), the first conductor plate 452 has a characteristic signal response profile that is distinct from a baseline signal response, which is similar to the response of FIGS. 7A and 7B. In the instance of FIGS. 8A and 8B, the signal processor 410 compares the conditioned signal to the baseline signal and the determinator 414 determines that a root 142 is detected between the first conductor plate 452 and the second conductor plate 654 because the conditioned response signal is distinct from the baseline signal response (e.g., signal response without a root present). In some examples, determinator 414 is a digital comparator configured to determine whether the difference between portions of the conditioned signal response and portions of the baseline signal response exceeds a threshold value. For instance, the determinator 414 can determine that a root is detected when a peak of the response signal exceeds a threshold value (e.g., 90% of peak from baseline signal). In another instance, the determinator 414 can determine that a root is detected when a peak of the response signal drops below a threshold value (e.g., 90% of peak from baseline signal).

Figure 9A:
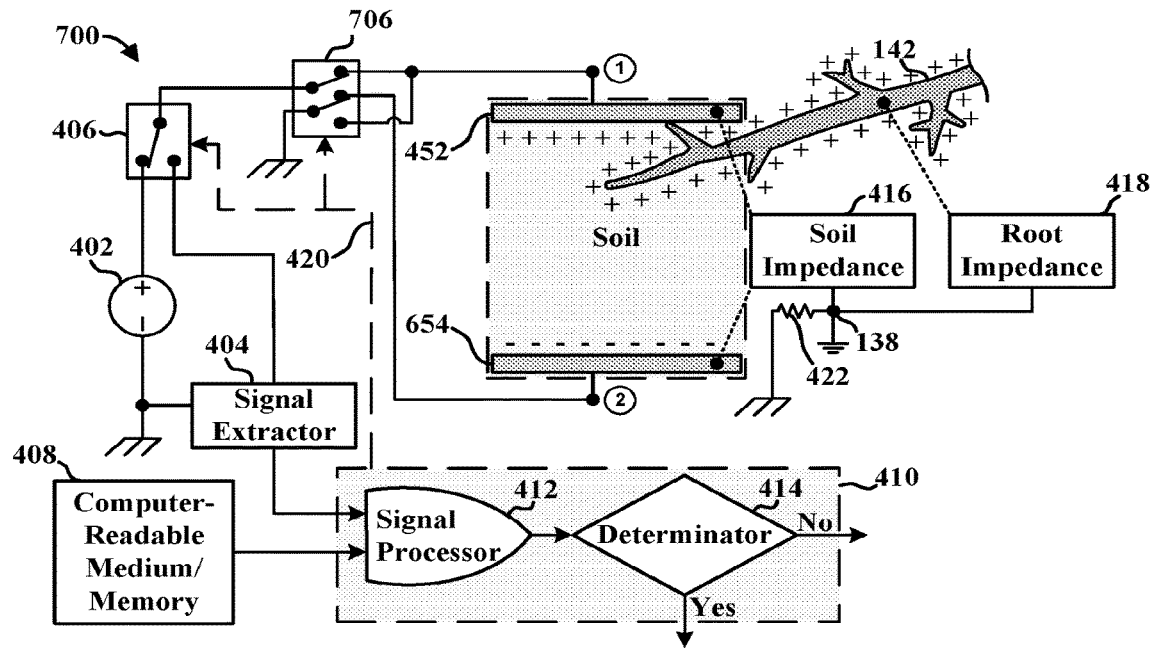
FIGS. 9A and 9B are circuit diagrams illustrating an example of a root proximity sensor configured to determine whether a root is between the first conductive plate and the second conductor plate at instances when a root impinges on at least one conductor plate.
Figure 9B:
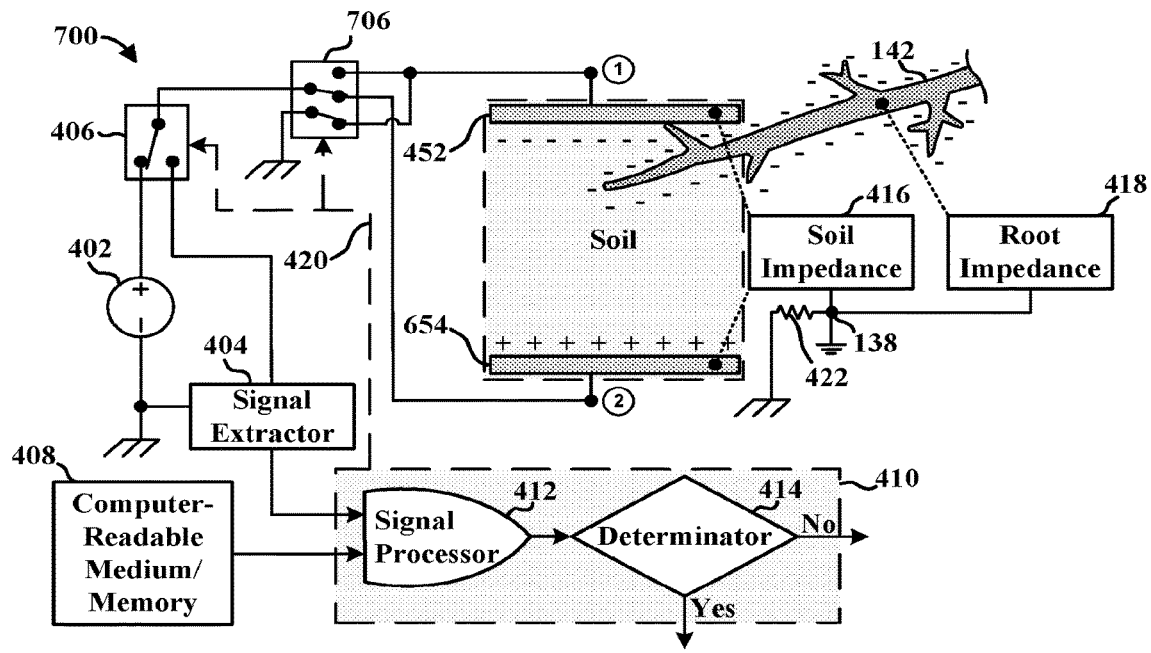

FIGS. 9A and 9B are circuit diagrams illustrating an example of a root proximity sensor configured to determine whether a root is between a first conductive plate 452 and a second conductor plate 654 at instances when a root impinges on at least one conductor plate. The proximity sensor 700 has the same components as described in FIGS. 7A, 7B, 8A, and 8B above. As depicted in FIG. 9A, the root 142 is in contact with the first conductor plate 452. As such, the charge on the first conductor plate 452 is distributed throughout root 142. The distribution of charge provides an additional electrical path (e.g., root impedance 418) for dissipation. In this example, the charge is no longer confined to the first conductor plate 452 for dissipation through the soil (e.g., soil impedance 416 path). Instead, the charge is distributed along the root 142 (e.g., root impedance 416 path), which changes the characteristic signal response profile from the baseline signal response.

Consequently, the overall impedance of the soil between the first conductor plate 452 and the second conductor plate 654 becomes the capacitance of the soil $C_{soil}$ in parallel with the overall capacitance of the root $C_{root}$ in parallel with the resistance of the soil $R_{soil}$ in parallel with the overall resistance of the root $R_{root}$, as depicted in FIG. 8B. In some examples, the overall impedance decreases between the first conductive plate 452 and the second conductor plate 654. It should be appreciated that the capacitance of the soil $C_{soil}$, the overall capacitance of the root $C_{root}$, the resistance of the soil $R_{soil}$, and the overall resistance of the root $R_{root}$ can vary based on the resistivity, salinity, moisture content, temperature, aeration, aggregation (e.g., rocky, clay, sand), and the like. Likewise, the values for the $C_{soil}$ in parallel with the overall capacitance of the root $C_{root}$ in parallel with the resistance of the soil $R_{soil}$ in parallel with the overall resistance of the root $R_{root}$ between the configuration depicted in FIG. 8A can be different from the values of the $C_{soil}$ in parallel with the overall capacitance of the root $C_{root}$ in parallel with the resistance of the soil $R_{soil}$ in parallel with the overall resistance of the root $R_{root}$ for the configuration depicted in FIG. 9.

It should be appreciated that earth ground and chassis ground can have different voltage potentials (e.g., $V_{Earth} \neq V_{chassis}$). That is, even for instances where an electrical wire shorts the chassis ground to earth ground, the electrical wire connection has a non-zero line impedance 422. In some instances of poor grounding, the electrode 138 can be positioned on the chassis ground rather than the earth ground depicted in FIGS. 9A and 9B.

As depicted in FIGS. 7A, 7B, 8A, and 8B, the root proximity sensor 700 can optionally include a polarity switch 706 electrically coupled to switch 406, the first conductor 452 and the second conductor 654. The polarity switch is configured to provide a second configuration that exchanges electrical coupling between the first conductor plate 452 and the second conductor plate 654. That is, the polarity switch 706 reconfigures the electrical coupling such that the first conductor plate 452 is electrically coupled to ground (e.g., chassis ground) and the second conductor plate 654 is electrically connected to the power supply 402 in the first mode or the signal extractor 404 through the switch 406 in the second mode.

FIG. 9B depicts an instance with the polarity switch 706 thrown such that the first conductor plate 452 is electrically coupled to ground (e.g., chassis ground) and the second conductor plate 654 is electrically coupled to the power supply 402 in the first mode of the switch 406 while the root 142 is in contact with the first conductor plate 452. In such an instance, the electrons from the first conductor plate 452 are distributed throughout root 142 causing the root to be grounded (or close to being grounded). It has been found that the distribution of the electrons along root 142 further assists in grounding and weakly affects additional electrical distribution paths (e.g., root impedance 418). The reason is attributed to the positive charge being confined to the second conductor plate 654 for dissipation through the soil (e.g., soil impedance 416 path), which is substantially similar to the characteristic signal response profile from the baseline signal response (e.g., signal response without the root 142).

The difference in signal profile from the configuration of FIG. 9A compared to the configuration of FIG. 9B is that it provides a symmetry metric. That is, a root 142 in contact with the first conductor plate 452, as depicted in FIG. 9A, provides a signal profile characteristic of a root's presence. The polarity switch 706 configured as depicted in FIG. 9B does not provide a signal profile characteristic of a root's presence. Likewise, a root 142 in contact with the second conductor plate 654 provides a signal profile characteristic of a root's presence when the polarity switch 706 is configured such that the first conductor plate 452 is electrically coupled to ground (e.g., chassis ground) and the second conductor plate 654 is electrically connected to the power supply 402 in the first mode or the signal extractor 404 through the switch 406 in the second mode. Whereas the polarity switch 706 is configured such that the second conductor plate 654 is electrically coupled to ground (e.g., chassis ground) and the first conductor plate 452 is electrically connected to the power supply 402 in the first mode of the switch 406 in the second mode, which does not substantially provide a signal profile characteristic of a root's presence.

FIGS. 10A-10C are diagrams illustrating an example of a non-invasive root phenotyping device 600 with a plurality of parallel conductor plates 626 surrounding a plant at various stages of growth of a plant root system over time 1000A, 1000B, 1000C. As depicted in FIGS. 10A-10C, the root phenotyping device 600 includes a plurality of parallel conductor plates 626 affixed to a portion of sensor array 625, which are extended around the circular supports 122A, 122B, 122C to enclose a cylindrical surface around the plant 140. The portion of sensor array 625 is trellised to cage structure 120 and is similar to the root phenotyping device 600 depicted in FIG. 6. Although a single portion of sensor array 625 is depicted, portions of sensor array 625 are intended to be disposed in each space between vertical supports and circular supports 122A, 122B, 122C.

At time 1000A, seed 540 is planted in a soil at a specified location at a known depth. The root phenotyping device 600 is buried around this soil location such that the location of seed 540 is at or near an approximate center of cage structure 120. In some examples, the root phenotyping device 600 can be buried prior to time 1000A depicted in FIG. 10A. For example, multiple root phenotyping devices 600 can be installed along a row, at an instance in time, and individual seeds 540 can be planted at or near the center of each root phenotyping device 600 at a later instance in time using an automated planter. In some instances, root phenotyping device 600 can be buried after seed 540 has been planted without interfering with the roots 142. For example, root phenotyping device 600 can be buried while plant 140 is at a stage in growth similar to that depicted in FIG. 5B.

FIG. 10B represents a later time than FIG. 10A, where the seed 540 has sprouted and has grown into a small plant with relatively small roots 142 that emanate from the known planted location. In this instance, the roots 142 emanate from the plant 140 at or near the origin of where the seed 540 had been planted in FIG. 10A. As depicted in FIG. 10B, the root phenotyping device 600 does not detect a root 142 presence because the roots do not touch either the first conductor plate 452 or the second conductor plate 654 of the proximity sensor 700. Likewise, the roots 142 have not grown between the first conductor plate 452 and the second conductor plate 654 of the proximity sensors.

FIG. 10C represents a later time than FIG. 10B, where the plant 140 and the roots 142 have grown. In this instance, the roots 142 have grown sufficiently to touch either the first conductor plate 452 or the second conductor plate 654 of the proximity sensors of at least a portion of sensor array 625. Likewise, the roots 142 have grown sufficiently to be disposed between the first conductor plate 452 and the second conductor plate 654 of the parallel conductor plates 626 or at least a portion of sensor array 625. In such an instance, the parallel conductor plate 626A1 has a root 142 touching the second contact plate 654. Also, the parallel conductor plate 626A1 has a root 142 between the first conductor plate 452 and the second conductor plate 654. Consequently, the extracted signal response is conditioned (e.g., via signal processor 412) and compared to a baseline signal response (e.g., via determinator 414) and determined by the microcontroller 410 that a root 142 is in proximity with parallel conductor plate 626A1 and parallel conductor plate 626A5 at a designated time (e.g., timestamp).

In some instances, the parallel conductor plates 626 of proximity sensor 700 do not detect a root 142 below the parallel conductor plates 626A1-X (e.g., no root at parallel conductor plates 626B1-X, 626C1-X, etc.). In such an instance, the root phenotyping devices 600 can determine the root approximate growth rate (e.g., distance to parallel conductor plates 626A1, 626A5 divided by the time of initial detection) as well as the approximate depth of the root system.

Figure 11:
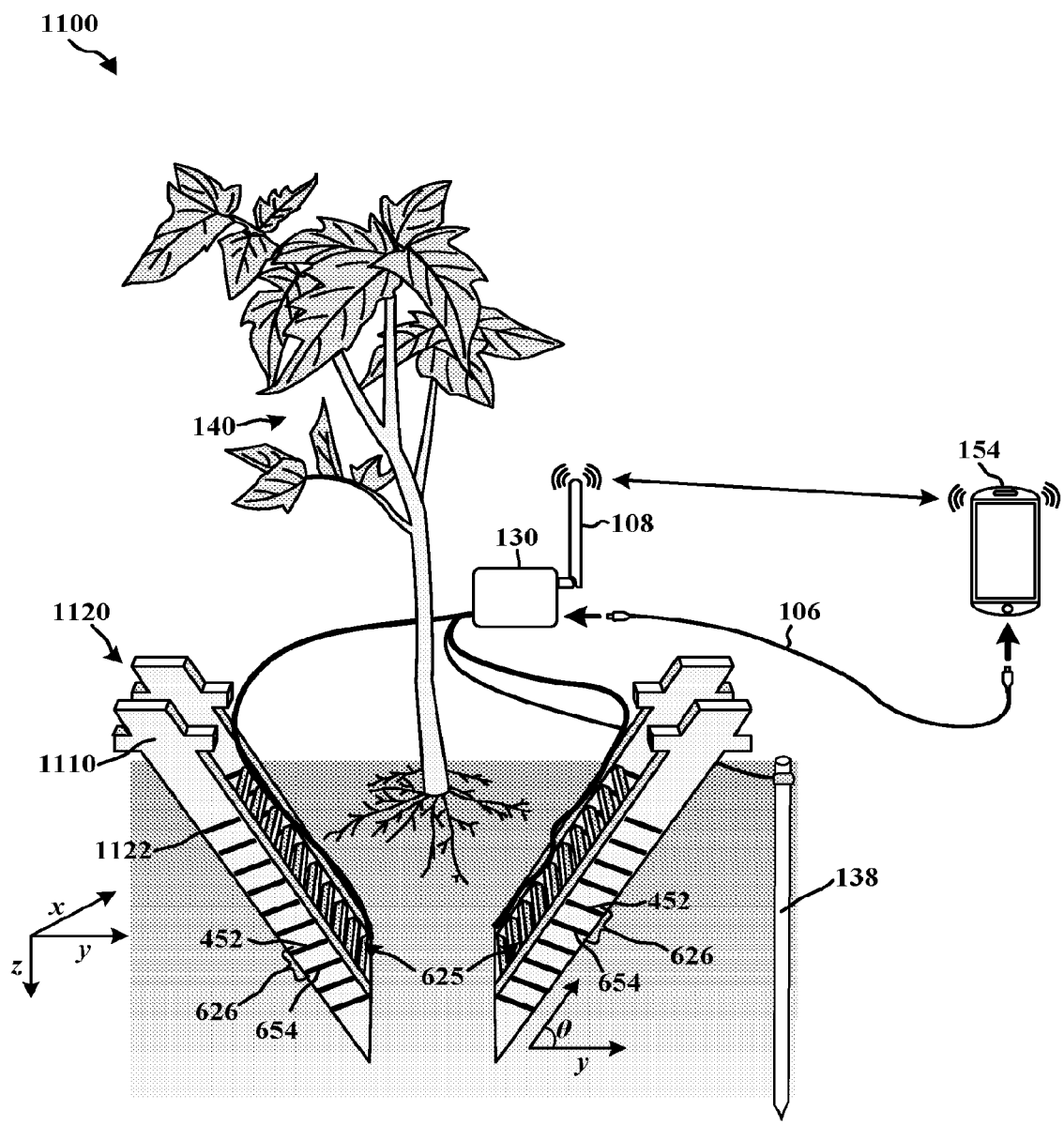
FIG. 11 is a diagram illustrating an ISO-view of a non-invasive root phenotyping device with a proximity sensor array with a plurality of proximity sensors trellised on a stake.

FIG. 11 is a diagram illustrating an ISO view of a non-invasive root phenotyping device 1100 with a proximity sensor array 625 and a plurality of proximity sensors trellised on a stake 1120. The stake 1120 is a support structure suitable for arrangement in a soil location adjacent to plant 140. In this example, the support structure is a planar structure with a lateral support 1122 vertically connected between vertical supports 1110, which forms a backbone for the support structure. In some examples, the support structure is made from any material that resists deformation upon insertion into a desired soil type without affecting the health and growth of the plant 140. For example, the material of the support structure of a stake 1120 can be a metal (e.g., galvanized steel, stainless steel), a plastic (e.g., bioplastics), and the like. In some examples, the material of the support structure of a stake 1120 is made from biodegradable and/or compostable material such as polylactic acid (PLA), poly-3-hydroxybutyrate (PHB), polyhydroxyalkanoates (PHA), and the like. In some instances, a 3-D printer can be utilized to construct the support structure of a stake 1120 using a suitable thermoplastic (e.g., PLA, etc.). In some instances, the support structure of a stake 1120 can be injected molded using a suitable thermoplastic (e.g., PLA, etc.)

The root phenotyping device 1100 further includes a plurality of parallel conductor plates 626 and/or conductor plates 126 affixed to the support structure (e.g., support structure of stake 1120). For example, the plurality of sensors is a plurality of parallel conductor plates 626 that are trellised between the adjacent lateral supports 1122. In some examples, the plurality of sensors is a plurality of conductor plates 126 affixed to the lateral support 1122. In some examples, the plurality of sensors is a plurality of conductor plates 126 affixed to the vertical supports 1110. In some examples, the plurality of sensors is a plurality of parallel conductor plates 626 with the first conductor plate 452 and the second conductor plate 654 affixed to the vertical supports 1110 and/or the lateral supports 1222. The extended vertical supports 1110 provide for a relatively fixed position during insertion into a soil location and subsequent operation. In some instances, one or more of the plurality of conductor plates 126 can be provided on a mesh that is positioned between the vertical supports 1110 and the lateral supports 1222.

As depicted in FIG. 11 the stake 1120 is tilted at an angle $\theta_2$ with respect to the base of the root 142. In some examples, the conductor plates 126 are oriented substantially parallel to the base of a root 142. In some examples, the conductor plates 126 are tilted at oblique angles with respect to the base of a root 142. That is, the conductor plates 126 are situated at a slant from the +y direction (e.g., y axis) toward the +z direction (e.g., z axis) with respect to a lateral (x-y plane) base of the root 142.

Each of the plurality of conductor plates 126 is electrically coupled (e.g., via wired interconnects) to a controller 130 (e.g., microcontroller) that is configured to determine whether a root is present in proximity to a conductor plate 126. As depicted in FIG. 11, controller 130 includes a communications unit (e.g., antenna 108, I/O port for cable 106) configured to transmit sensory data to a mobile device 154 (e.g., smart phone, tablet PC). In some instances, the communications unit can transmit sensory data over cable 106 to a mobile device 154. In some instances, cable 106 is a serial cable with appropriate connectors to interface with the communication unit of controller 130 and the mobile device 154. In such an instance, the communication unit includes circuitry (e.g., serial transceiver, etc.) to transmit and receive serial communications. In some examples, the communications unit can include an antenna 108 and circuitry configured to transmit sensory data wirelessly (e.g., Bluetooth, WiFi) to mobile device 154. In such an instance, the communication unit includes circuitry (e.g., Bluetooth transceiver, WiFi transceiver, etc.) to transmit and receive communications via wireless protocols. In some examples, the communications unit can include an antenna 108 and circuitry configured to transmit sensory data over a cellular network (e.g., 3G, 4G, LTE) to cellular tower or mobile device 154. In such an instance, the communication unit includes circuitry (e.g., 3G transceiver, 4G transceiver, LTE transceiver, etc.) to transmit and receive communications via cellular protocols.

It should be appreciated that the root phenotyping device 1100 can also include one or more sensors (e.g., soil sensor 134, ambient sensor 136) associated with any desired aspect of plant 140, the soil location, and/or one or more above-ground conditions at or near the soil location. Similarly, it should be appreciated that the root phenotyping device 1100 can include additional stakes 1120 to surround the plant 140. In some examples, the stakes include interlocking mechanisms that guide positioning of adjacent stakes 1120. In some examples, the stakes form a cage structure that surrounds the plant 140.

Figure 12:
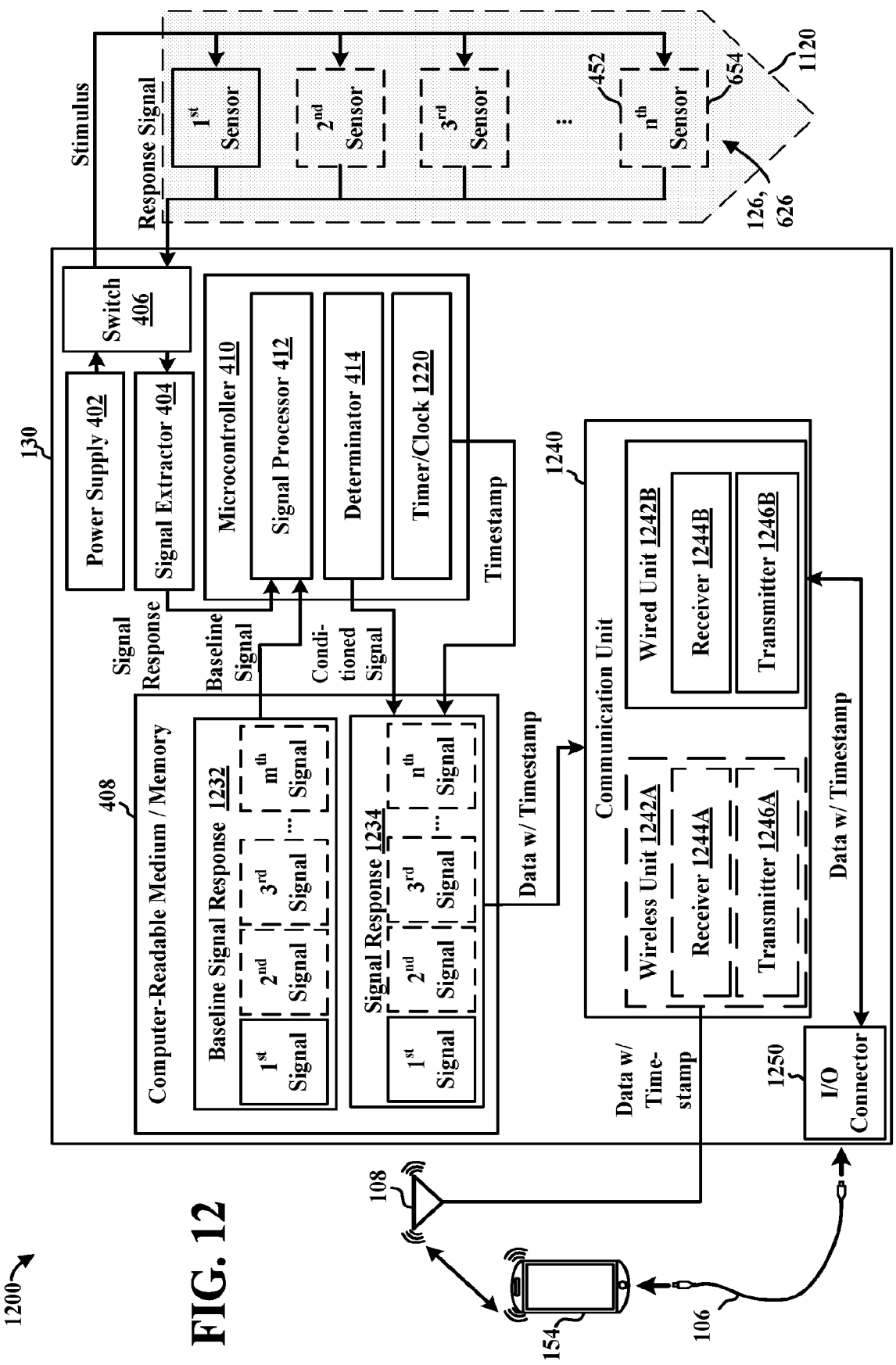
FIG. 12 is a conceptual data flow diagram illustrating the data flow between different means/components at a root phenotyping device.

FIG. 12 is a conceptual data flow diagram illustrating the data flow between different means/components at a root phenotyping device 1200. The root phenotyping device 1200 is for monitoring growth of a root of a plant in a soil location and can be the root phenotyping device 100 depicted in FIG. 1, the root phenotyping device 600 depicted in FIG. 6, or the root phenotyping device 1100 depicted in FIG. 11.

As depicted in FIG. 12, the controller 130 of the root phenotyping device 1200 includes a power supply 402, signal extractor 404, microcontroller 410, computer readable medium/memory 408, a communication unit 1240, and an I/O connector 1250. Microcontroller 410 further includes a signal processor 412, a determinator 414, and a timer/clock 1220.

The communication unit 1240 includes a wireless unit 1242A and a wired unit 1242B. The wireless unit 1242A has a transmitter 1246A and receiver 1244A configured to transmit sensory data to a mobile device 154 (e.g., smart phone, tablet PC). The communications unit 1240 can include an antenna 108 that, along with the transmitter 1246A and receiver 1244A, can transmit sensory data wirelessly (e.g., Bluetooth, WiFi) to mobile device 154. In some examples, the transmitter 1246A and the receiver 1244A transmit and receive communications via wireless protocols. In some examples, the transmitter 1246A and the receiver 1244A transmit and receive communications via cellular protocols over a cellular network (e.g., 3G, 4G, LTE). The wired unit 1242B has a transmitter 1246B and a receiver 1244B configured to transmit sensory data over cable 106 to a mobile device 154. In some examples, the cable 106 is a serial cable with appropriate connectors to interface with the I/O connector 1250 and the mobile device 154. In some examples, the transmitter 1246B and the receiver 1244B can transmit and receive serial communications.

The computer-readable medium/memory 408 can store one or more baseline signal responses 1232 (e.g., $1^{st}$ signal through $m^{th}$ signal) that are applicable to conditions in the soil. For example, one baseline signal response 1232 (e.g., $1^{st}$ signal) can be a signal response for wet, salty soils where the impedance can be low (e.g., resistivity ~10 Ω-m). Another baseline signal response 1234 (e.g., $2^{nd}$ signal) can be a signal response for dry soils where the impedance can be high (e.g., resistivity ~1 kΩ-m). Another baseline signal response 1232 (e.g., $1^{st}$ signal) can be a signal response for very dry soils where the impedance can be even higher (e.g., resistivity ranging between 1 kΩ-m to 10 kΩ-m).

The computer-readable medium/memory 408 can store also one or more signal responses 1234 (e.g., $1^{st}$ signal through $n^{th}$ signal) that are applicable to conditions in the soil. For example, one signal response 1234 (e.g., $1^{st}$ signal) can be a signal response for wet salty soils where the impedance can be low (e.g., resistivity ~10 Ω-m). Another signal response 1234 (e.g., $2^{nd}$ signal) can be a signal response for dry soils where the impedance can be high (e.g., resistivity ~1 kΩ-m). Another signal response 1234 (e.g., $1^{st}$ signal) can be a signal response for very dry soils where the impedance can be even higher (e.g., resistivity ranging between 1 kΩ-m to 10 kΩ-m).

In one configuration, the root phenotyping device 1200 includes an electronic sensor for detecting a root of a plant 140 in soil. The electronic sensor is a contact sensor 400 (of FIG. 4) that includes a first conductor plate 452 configured to be disposed in soil, a switch 406, a signal extractor 404, and a power supply 402. The switch 406 is configured to switch between a first mode and a second mode. The power supply 402 is electrically coupled to the switch 406 and the power supply 402 is configured to provide an electrical charge to the first conductor plate 452 in the first mode of the switch 406. The signal extractor 404 is electrically coupled to the switch 406 and the signal extractor 404 is configured to capture a signal response 1234 at the first conductor plate 452 in the second mode of the switch 406. In some examples, the signal extractor 404 is a voltage divider. In some examples, the signal extractor 404 is an analog to digital converter.

The electronic sensor further includes a microcontroller 410 electrically coupled to the signal extractor 404 and a computer readable medium/memory 408 electrically coupled to the microcontroller 410. As depicted in FIG. 12, the microcontroller 410 further includes a signal processor 412, a determinator 414, and a timer/clock 1220. The memory is configured to store data associated with the signal extractor 404. The signal processor 412 of the microcontroller 410 is configured to receive the signal response 1234 from the signal extractor 410. In some examples, the signal processor 412 of the microcontroller 410 is configured to retrieve a baseline signal response 1232 from computer readable medium/memory 408.

In some examples, the determinator 414 of the microcontroller 410 is configured compare the signal response to the baseline signal response 1232 to determine whether a difference between a portion of the signal response and a portion of the baseline signal 1232 response exceeded a threshold value. In such an instance, the presence of a root 142 is associated with a determination that the signal response 1232 exceeded the threshold value.

In another configuration, the electronic sensor is a proximity sensor 700 (of FIG. 7) that further includes a second conductor plate 654 configured to be disposed in soil adjacent to and substantially parallel to the first conductor plate 452. The second conductor plate 654 is electrically coupled to ground (e.g., earth ground and chassis ground). In some examples, a gap between the first conductor plate 452 and the second conductor plate 654 has a cross sectional area of less than or equal to about 1 cm². In some configurations, a distance between the first conductor plate 452 and the second conductor plate 654 is equal to or greater than about 1 mm. In some examples, the electronic sensor further includes a polarity switch 706 configure to exchange electrical coupling between the first conductor plate 452 and the second conductor plate 654.

In some examples, the switch 406 is a multiplexer that is electrically coupled to and controlled by the microcontroller 410. In some examples, the switch 406 is a relay that is electrically coupled to and controlled by the microcontroller 410. In some examples, the electronic sensor further includes a soil humidity sensor (e.g., soil sensor 134) or a temperature sensor (e.g., ambient sensor 136) electrically coupled to the microcontroller 410. In some examples, the electronic sensor is oriented at an oblique angle with respect to a lateral of a root base. In some examples, the electronic sensor is affixed to a mesh suspended between members of support structure (e.g., vertical supports 110 and circular supports 122A, 122B, 122C). In some examples, the baseline signal response 1232 is representative of a signal response 1234 of the electronic sensor in soil without a root 142 disposed between the first conductor plate 452 and the second conductor plate 654 or without a root 142 that is in contact with either the first conductor plate 452 or the second conductor plate 654. In some examples, the signal response 1234 is stored in the computer readable medium/memory 408 at predetermined (e.g., periodic) intervals.

In another configuration, the root phenotyping device 1200 is an electronic device for monitoring growth of a root of a plant 140 in a soil location. The electronic device includes a support structure (e.g., cage structure 120, stake 1120, auger) suitable for arrangement adjacent to the soil location. The electronic device further includes a plurality of electronic sensors affixed to the support structure.

At least one of the plurality of sensors is a contact sensor 400 that includes a first conductor plate 452, a switch 406, a signal extractor 404, and a power supply 402. The switch 406 is configured to switch between a first mode and a second mode. The power supply 402 is electrically coupled to the switch 406 and the power supply 402 is configured to provide an electrical charge to the first conductor plate 452 in the first mode of the switch 406. The signal extractor 404 is electrically coupled to the switch 406 and the signal extractor 404 is configured to capture a signal response 1234 at the first conductor plate 452 in the second mode of the switch 406. In some examples, the signal extractor 404 is a voltage divider. In some examples, the signal extractor 404 is an analog to digital converter.

The electronic device further includes a microcontroller 410 electrically coupled to the signal extractor 404 and a computer readable medium/memory 408 electrically coupled to the microcontroller 410. As depicted in FIG. 12, the microcontroller 410 further includes a signal processor 412, a determinator 414, and a timer/clock 1220. The memory is configured to store data associated with the signal extractor 404. The signal processor 412 of the microcontroller 410 is configured to receive the signal response 1234 from the signal extractor 410. In some configurations, the signal processor 412 of the microcontroller 410 is configured to retrieve a baseline signal response 1232 from computer readable medium/memory 408.

In some examples, the determinator 414 of the microcontroller 410 is configured to compare the signal response to the baseline signal response 1232 to determine whether a difference between a portion of the signal response and a portion of the baseline signal 1232 response exceeded a threshold value. In such an instance, the presence of a root 142 is associated with a determination that the signal response 1232 exceeded the threshold value.

In some examples, at least one of the plurality of sensors is a proximity sensor 700 that further includes a second conductor plate 654 adjacent to and substantially parallel to the first conductor plate 452. The second conductor plate 654 is electrically coupled to ground (e.g., earth ground and chassis ground). In some examples, a gap between the first conductor plate 452 and the second conductor plate 654 has a cross sectional area of less than or equal to about 1 cm². In some configurations, a distance between the first conductor plate 452 and the second conductor plate 654 is equal to or greater than about 1 mm. In some examples, the electronic device further includes a polarity switch 706 configured to exchange electrical coupling between the first conductor plate 452 and the second conductor plate 654.

In some examples, the switch 406 is a multiplexer that is electrically coupled to and controlled by the microcontroller 410. In some examples, the switch 406 is a relay that is electrically coupled to and controlled by the microcontroller 410. In some examples, the electronic device further includes a soil humidity sensor (e.g., soil sensor 134) or a temperature sensor (e.g., ambient sensor 136) electrically coupled to the microcontroller 410. In some examples, at least one of the plurality of sensors is oriented at an oblique angle with respect to a lateral of a root base. In some examples, at least one of the plurality of sensors is affixed to a mesh suspended between members of the support structure (e.g., vertical supports 110 and circular supports 122A, 122B, 122C). In some examples, the baseline signal response 1232 is representative of a signal response 1234 of the electronic sensor in soil without a root 142 disposed between the first conductor plate 452 and the second conductor plate 654 or without a root 142 that is in contact with either the first conductor plate 452 or the second conductor plate 654. In some examples, the signal response 1234 is stored in the computer readable medium/memory 408 at predetermined (e.g., periodic) intervals.

Figure 13:
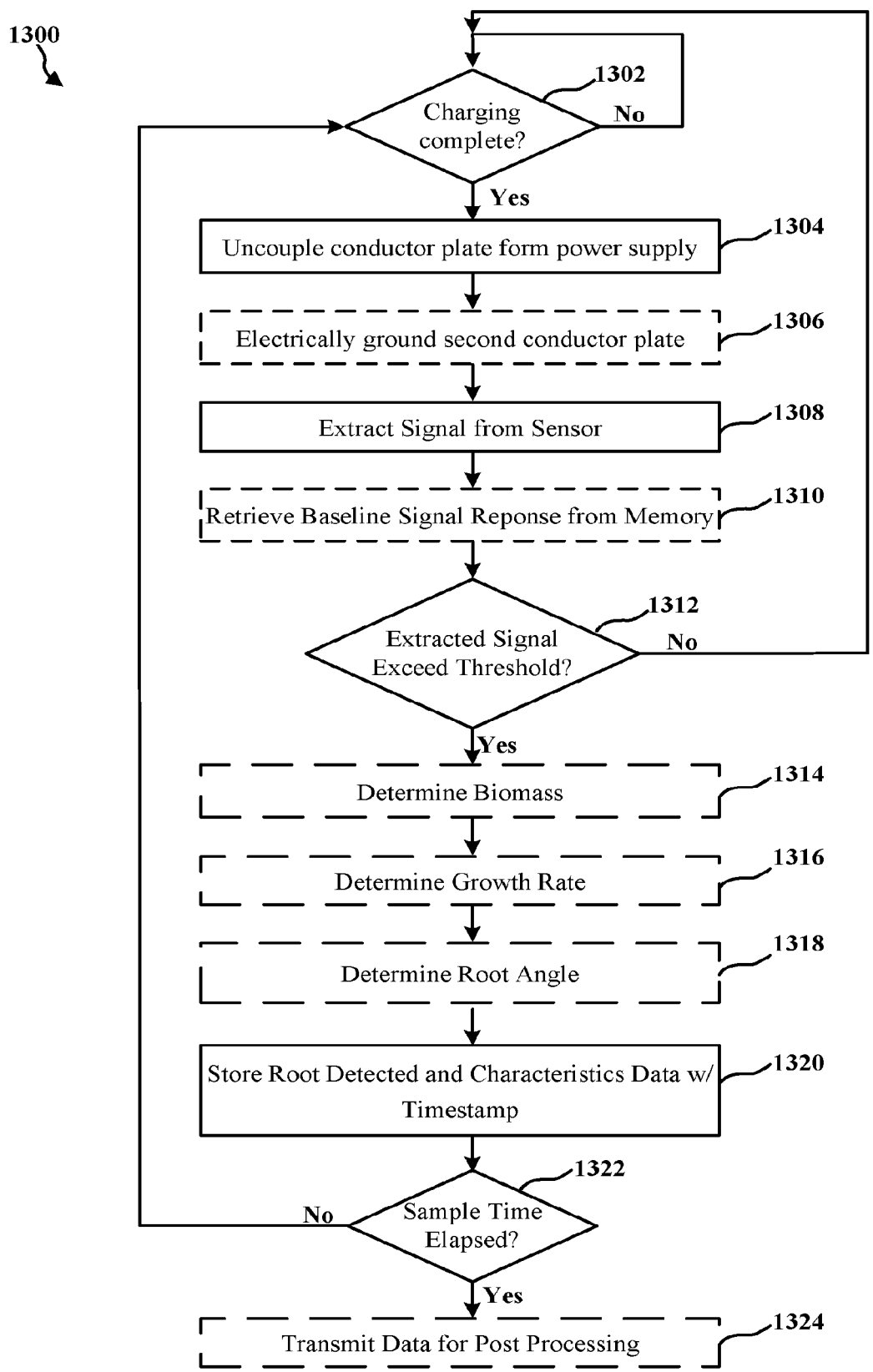
FIG. 13 is a flow diagram of a plant phenotyping device with a plurality of sensors to detect roots and determine root traits.

FIG. 13 is a flow diagram 1300 of a plant phenotyping device with a plurality of sensors to detect roots 142 and determine root traits. The plant phenotyping device can be the non-invasive root phenotyping device 100, non-invasive root phenotyping device 600, or non-invasive root phenotyping device 100. The root phenotyping device is configured to detect and to monitor a root presence at a conductor plate 126 and store the location in computer readable medium/memory 408 along with other characteristic data (e.g., temperature, soil resistivity, soil humidity, ambient humidity, ambient temperature, timestamp, etc.).

At block 1302 the plant phenotyping device (e.g., non-invasive root phenotyping device 100, 600, 1100, etc.) electrically charges a first conductor plate 452 from a power supply 402 over a first predetermined time and determines whether the charging is complete. For example, the switch 406 can be thrown to a first mode in which the power supply 402 is electrically coupled to provide an electrical charge to the first conductor plate 452, as depicted in FIG. 4A and FIG. 7A. In some instances, the first predetermined time exceeds a time constant associated with soil impedance 416 between the first conductor plate 452 and an earth ground electrode 138. In some instances, the predetermined time can be an adjustable configuration to the plant phenotype device.

At block 1304 the plant phenotyping device (e.g., non-invasive root phenotyping device 100, 600, 1100, etc.) electrically uncouples the first conductor plate 452 from the power supply 402. For example, the switch 406 can be thrown to a second mode in which the signal extractor 404 is enabled to capture the signal response 1234. That is, the power supply 402 is electrically uncoupled from the first conductor plate 452 and the signal extractor 404 is electrically coupled to the first conductor plate 452.

At block 1306 the plant phenotyping device (e.g., non-invasive root phenotyping device 100, 600, 1100, etc.) electrically grounds a second conductor plate 654. The second conductor plate 654 is adjacent to and substantially parallel to the first conductor plate 452. It should be recognized that this is optional for contact sensors 400 and particular to proximity sensor 700. For proximity sensors 700, which includes a second conductor plate 654 the second conductor plate 654 is grounded to chassis ground prior to extracting measurements. The grounded second conductor plate 654 provides a reference ground plane for the first conductor plate 452 to facilitate signal response profiles.

At block 1308 the plant phenotyping device (e.g., non-invasive root phenotyping device 100, 600, 1100, etc.) extracts a signal response 1234 at the first conductor plate 452 over a second predetermined time. That is, the charge applied to the first conductor plate 452 dissipates over time as electrons flow from the earth ground of the electrode 138 through the soil to the first conductor plate 452. While the first conductor plate 452 is discharging signal extractor 404 can extract charge or voltage levels. This yields a signal response 1234 proportional to electrical properties of the soil (e.g., soil impedance 416). In some examples, the signal extractor is a voltage divider, where the extracted voltage is a ratio of impedances (e.g., $v_0 = Z_1/(Z_1+Z_2) \times v_{in}$).

In some examples, signal extractor 404 is an ADC configured to convert the signal response to digital equivalents. In such an example, the ADC can be configured to digitally capture the signal response. It should be appreciated that the extracted signal (e.g., voltage) from the ADC is with respect to the chassis ground of controller 130, which is common to a plurality of conductor plates 126. In some examples, the second predetermined time exceeds a time constant associated with soil impedance 416 between the first conductor plate 452 and an earth ground electrode 138. In some examples, the second predetermined time is adjustable.

In addition, signal processor 412 can condition the response signal 1234 so that it is more suitable for comparison. For example, the response signal 1234 can have high-frequency noise, and the signal processor 412 can apply a low-pass filter (e.g., Butterworth filter, Chebyshev filter, Cauer filter, etc.) to condition the signal response 1234.

At block 1310, the plant phenotyping device (e.g., non-invasive root phenotyping device 100, 600, 1100, etc.) retrieves the baseline signal response 1232 from computer readable medium/memory 408. For example, the signal processor 412 can retrieve from the computer readable medium/memory 408 (e.g., query a database), a baseline response signal 1232 for a soil that has similar resistivity and temperature to compare with the conditioned signal response. It should be appreciated that additional soil characteristics can also be applied when determining a baseline response signal such as salinity, aeration, etc.

At block 1312, the plant phenotyping device (e.g., non-invasive root phenotyping device 100, 600, 1100, etc.) determines whether a portion of the signal response 1234 exceeds a threshold value. A root presence is associated with a determination that the portion of the signal response 1234 exceeded the threshold value. For example, the plant phenotyping device can include a microcontroller 410 with a determinator 414 that compares the signal response 1234 to the baseline signal response 1232 to determine whether a root 142 is present.

In some examples, determinator 414 is a digital comparator configured to determine whether the difference between portions of the (conditioned) signal response 1234 and portions of the baseline signal response 1232 exceeds a threshold value. In one instance, a portion of the baseline signal response 1232 can be a peak (e.g., max or relative max value) that corresponds to a peak (e.g., max or relative max value) of the signal response 1234. In such an instance, the determinator 414 can determine that no root 142 is detected for a peak of the signal response 1234 exceeding a threshold value (e.g., 90% of peak from baseline signal).

At block 1314, the plant phenotyping device (e.g., non-invasive root phenotyping device 100, 600, 1100, etc.) determines the biomass in accordance with the signal response 1234 exceeding a threshold value (e.g., root detected). The biomass is proportional to a capacitance magnitude of the signal response 1234. In some examples, the biomass growth rate is proportional to the change in biomass over an elapsed time.

In some examples, each detected root 142, among the plurality of sensors, can be spatially mapped (e.g., to form a biomass map). In some examples, before the sensory data is mapped to biomass, it is preprocessed to identify errant data or missing data, perhaps caused by device malfunction or environmental conditions. In such examples, the accuracy is improved as some biomass data may not correspond to root biomass due to measurement error.

In some examples, a dynamic linear model with heteroskedastic errors is used to infer the latent (unobserved) root biomass evolution. In some instances, the latent root biomass is stored as a three dimensional array indexed by observation number, level, and level offset (e.g., designated 626A1-626A5, 626B1-626B5, 626C1-626C5 etc. positions) In some instances, residual heteroskedasticity is used to search for transient processes, like soil organisms such as worms or insects coming in contact with the device. Very large residuals indicate the presence of such soil organisms. In some instances, the underlying parameters of the model are adapted through standard statistical techniques.

At block 1316, the plant phenotyping device (e.g., non-invasive root phenotyping device 100, 600, 1100, etc.) determines the growth rate in accordance with the signal response 1234 exceeding a threshold value (e.g., root detected). The root growth rate is proportional to a three-dimensional coordinate of the conductor plate 126 over an elapsed time. For example, a timestamp of a positive detection can be compared against a timestamp of the seed 540 planting, or other reference timestamp, to determine a growth duration, which is then used to factor growth rate in conjunction with the root length determination.

Other growth rates are contemplated and can be extrapolated from data. For example, a local rate of growth can be determined by the incremental increase of biomass of each newly positive detected root 142. Likewise, a global rate of growth can be determined by the rate at which the root 142 are coming into contact with sensors at each different level (e.g., corresponding to different root lengths). As such, properties of individual roots and global RSA properties can be calculated.

As part of the growth rate, the root length can also be calculated. For example, a three-dimensional coordinate of the sensor (e.g., conductor plate 126 or parallel conductor plate 626) can provide an approximate root length from the coordinate of the seed 540 location. This provides an inference of global RSA growth based on knowledge about the proportion of roots that are likely to come in contact with a sensor (e.g., conductor plate 126 or parallel conductor plate 626).

At block 1318, the plant phenotyping device (e.g., non-invasive root phenotyping device 100, 600, 1100, etc.) determines the root angle in accordance with the signal response 1234 exceeding a threshold value (e.g., root detected). The root angle is based on an angle between a point of origin (e.g., origin of the seed) or a crown of the plant root 142 and a three-dimensional coordinate of the sensor (e.g., conductor plate 126 or parallel conductor plate 626).

In some examples, the root angle is determined by calculating the angle between the three-dimensional coordinate of the respective sensor (e.g., conductor plate 126 or parallel conductor plate 626) and the location in which the seed 540 was planted (or the location from which the plant root system emanates). The root phenotyping device 100, 600 of the present disclosure can dictate the soil location at which the seed 540 is planted. Hence, the point of origin (e.g., origin of the seed) of the root emanation location is calculated as a predetermined distance above the seed 540. The root emanation location, the radius of each level, and the depth of each level, can be used to calculate the amount of root biomass growing at certain altitude angles relative to the root emanation location.

In some instances, the root growth is not circularly symmetric (e.g., elliptical or oblong-shaped). The root emanation location and the sensor (e.g., conductor plates 126 or parallel conductor plates 626) locations can be used to record root growth at certain azimuth angles. In some instances, the sensor (e.g., conductor plate 126 or parallel conductor plate 626) locations summarize root growth in terms of the primary and secondary directions of variation perpendicular to the surface normal. In some examples, the total root biomass at each point in time can be converted to proportions of the root system growing at the each altitude angle over time.

Aspects of RSA, such as root angle (e.g., point of origin root angle), contribute to plant growth and nutrient acquisition. The correlation of the root angle to plant growth is particularly relevant to resource resistance. For example, steep-angled roots provide row to row crops such as maize access to ground water during droughts, whereas shallower roots increase the uptake of immobile nutrients found in shallow soils, such as phosphorus.

At block 1320, the plant phenotyping device (e.g., non-invasive root phenotyping device 100, 600, 1100, etc.) stores a root presence indicator to the computer readable medium/memory 408 in accordance with the portion of the signal response 1234 exceeding the threshold value. In some examples, additional information (e.g., soil resistivity, temperature, timestamp, signal response, coordinate location, etc.) are stored with the root presence indicator. In some examples, the root presence indicator is stored in a database.

At block 1322, the plant phenotyping device (e.g., non-invasive root phenotyping device 100, 600, 1100, etc.) determines whether the predetermined sample time has elapsed. In some examples, the sample time is the number of days for a particular crop season. In some examples, the root phenotyping device can be enabled to gather data indefinitely (e.g., gather data until user intervenes).

At block 1324, the plant phenotyping device (e.g., non-invasive root phenotyping device 100, 600, 1100, etc.) transmits data for post processing in accordance with the predetermined sample time that elapsed. In some examples, a cable 106 can be used to connect a mobile device 154 to the controller 130 (e.g., I/O connector 1250) and the data (e.g., root presence indicator, soil resistivity, temperature, timestamp, signal response, coordinate location, etc.) can be transmitted to the mobile device 154 for further processing. In some examples, that mobile device 154 can interface with the controller 130 wirelessly (e.g., Bluetooth, WiFi, etc.) and the data (e.g., root presence indicator, soil resistivity, temperature, timestamp, signal response, coordinate location, etc.) can be transmitted wirelessly to the mobile device 154 for further processing.

In some examples, the techniques of the present disclosure implement multiple non-invasive root phenotyping devices 100, 600, 1100. For example, as depicted in FIG. 11, the non-invasive root phenotyping device 1100 implements a two stakes 1120. The techniques can also implement two or more non-invasive root phenotyping device 100, 600, 1100 having different sizes around a single soil location. This facilitates the capture of additional root interactions over time, as compared to the use of a single device.

It should be appreciated that the techniques described above for monitoring growth of plant root(s) can be adapted for a variety of uses. The steps of positioning a plurality of sensors (e.g., conductor plate 126 or parallel conductor plate 626) around a soil location, planting a seed 540 in the soil location, receiving data representing a root presence, and determining a root growth characteristic of a plant root based on the data, as well as the optional features and elements, can find use, alone or in combination, with any of the techniques described herein.

Certain aspects of the present disclosure relate to techniques for selecting a plant for breeding based on a root growth characteristic. In some examples, the techniques include positioning a plurality of conductor plate 126 (e.g., for conductor plate 126 or parallel conductor plate 626) around a soil location, planting a seed 540 in the soil location, receiving data representing a root presence from a plant root 142 after the seed 540 has grown into a plant 140, determining a root growth characteristic of the plant root based on the data, and selecting the plant for breeding based on the determined root growth characteristic.

A variety of root growth characteristics, including, growth rate, root angle, root length, and root biomass, can be desirable characteristics for selection and breeding. In some examples, different root angles are advantageous for acquisition of different soil resources. For example, if a breeder wishes to maximize shallow resource uptake (e.g., phosphorus), the breeder to can select plants with shallower root angles. Likewise, if a breeder wishes to maximize deep resource uptake (e.g., nitrogen or water during drought conditions), the breeder can select plants 140 with deeper root angles. The techniques of non-invasive root phenotyping described herein allow for the real-time determination of a multitude of root growth characteristics, which enables large-scale screening and identification of plants or cultivars with desired or new root growth characteristics. This facilitates new hybrid cultivars as these cultivars can be tested against a commercial variety to determine whether the cultivars have different root growth characteristic.

In some examples, the techniques further include crossing the plant determined to have a particular root growth characteristic with a second plant of the same species to produce a progeny plant. In some examples, the second plant has the same root growth characteristic, thereby allowing the fixation of a characteristic of interest. In other examples, the second plant has a different desired root growth characteristic, thereby crossing multiple characteristics to achieve new and/or desirable permutations of RSA properties.

A number of selection and breeding techniques can be suitably used in the techniques of the present disclosure including, recurrent selection, mass selection, bulk selection, backcrossing, pedigree selection, modified pedigree selection, selfing, sibbing, hybrid production, crosses to populations, open pollination breeding, restriction fragment length polymorphism enhanced selection, genetic marker enhanced selection, making double haploids, and transformation, and the like. It should be appreciated that each technique can be implements alone or in combination with other techniques.

In some examples, the devices, techniques, and/or computer-readable storage media of the present disclosure can be used in the production of hybrid plant varieties. For example, varieties can be produced to introduce the traits or characteristics (e.g., one or more root growth characteristics of the present disclosure) of a variety into other lines, or provide a source of breeding material that can be used to develop new inbred varieties. The development of hybrids in a plant breeding program requires, in general, the development of homozygous inbred varieties, the crossing of these varieties, and the evaluation of the crosses. There are many analytical techniques to evaluate the result of a cross. Some techniques include the observation analysis of phenotypic traits, while other techniques include genotypic analysis.

In some examples, backcross breeding is implemented to transfer one or a few favorable genes for a highly heritable trait (e.g., a root growth characteristic of the present disclosure) into a desirable variety. This approach can be used for breeding disease-resistant varieties. Various recurrent selection techniques can be used to improve quantitatively inherited traits controlled by numerous genes. The use of recurrent selection in self-pollinating crops depends on the ease of pollination, the frequency of successfully pollinated hybrids, and the number of hybrid offspring from each successful cross. Promising advanced breeding lines can be thoroughly tested and compared to appropriate standards in environments representative of the commercial target area(s) for a designated period of time. The best lines can then be candidates for new commercial varieties. Those still deficient in a few traits can be further used as parents to produce new populations for additional selection.

In some examples, a breeding scheme includes crosses and/or selfing. For instance, a breeder can initially select and cross two or more parental lines, followed by repeated selfing and selection, to produce many new genetic combinations. Moreover, a breeder can generate multiple different genetic combinations by crossing, selfing, and mutations. A plant breeder can then select which germplasm to advance to the next generation. This germplasm can then be grown under different geographical, climatic, and soil conditions, and further selection can be made during, and at the end of, the growing season.

Pedigree breeding is generally used for the improvement of self-pollinating crops or inbred lines of cross-pollinating crops. Two parents that possess favorable, complementary traits are crossed to produce an F1. An F2 population is produced by selfing one or several F1's or by intercrossing two F1's (sib mating). Selection of the best individuals is usually begun in the F2 population. Then, beginning in the F3, the best individuals in the best families are selected. Replicated testing of families, or hybrid combinations involving individuals of these families, often follows in the F4 generation to improve the effectiveness of selection for traits with low heritability. At an advanced stage of inbreeding (i.e., F6 and F7), the best lines or mixtures of phenotypically similar lines are tested for potential release as new varieties.

Molecular markers can also be used during the breeding process for the selection of qualitative traits. Exemplary techniques for identifying molecular markers include, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARS), Amplified Fragment Length Polymorphisms (AFLPs), Simple Sequence Repeats (SSRs) and Single Nucleotide Polymorphisms (SNPs), to name a few. Markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent.

Mutation breeding can also be used to introduce new traits (e.g., one or more root growth characteristics of the present disclosure) into existing varieties. Mutations that occur spontaneously or are artificially induced can be useful sources of variety for a plant breeder. The goal of artificial mutagenesis is to increase the rate of mutation. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait can then be incorporated into existing germplasm by traditional breeding techniques.

In some examples, a plant 140 of the present disclosure is a row crop. In some examples, a plant 140 of the present disclosure is maize, soybean, rice, wheat, sorghum, tomato, or alfalfa. Other row crops include, without limitation, cotton, beets, grain hay, legumes (e.g., beans, peanuts, peas, etc.), flowers such as sunflowers, other grains (e.g., rye or oats), sugarcane, tobacco, kenaf, and the like.

Certain aspects of the present disclosure relate to techniques for determining an effect of a plant-microbe interaction on a root growth characteristic. It will be appreciated that such techniques are realized using the devices and techniques of the present disclosure in a variety of applications. In some examples, the techniques include positioning a plurality of sensors (e.g., conductor plate 126 or parallel conductor plate 626) around a soil location, planting a seed 540 in the soil location, inoculating the soil location with a microbe or community of microbes (or applying the microbe or community of microbes to the seed in the form of a seed treatment), after the seed 540 has grown into a plant 140 having a plant root 142, and after a plant-microbe interaction is established between the plant 140 and the microbe or community of microbes, receiving data representing a root presence, determining a root growth characteristic of the plant root based on the data, determining a reference root growth characteristic of a reference plant root from a reference plant of the same species as the first plant, and determining the effect of the plant-microbe interaction on the root growth characteristic by comparing the root growth characteristic to the reference root growth characteristic.

As used herein, a reference, when applied to a plant 140, plant root 142, and/or root growth characteristic, can refer to a plant 140, plant root 142, and/or root growth characteristic of a plant grown under a different condition as a plant of interest (e.g., a test plant). In some examples, the reference plant 140 is in a soil location not inoculated with the microbe or community of microbes. In some examples, the reference plant 14 is in a soil location not inoculated with any microbe. In some examples, the reference plant 140 is in a soil location inoculated with a different microbe or different community of microbes.

In some examples, the effect of a plant-microbe interaction on a root growth characteristic is determined by inoculating a soil location with a microbe of interest and studying its effect on root growth (e.g., as described above), thereby examining the effect of a particular, known microbe on root growth.

In other examples, the effect of a plant-microbe interaction on a root growth characteristic is determined by screening a variety of plants for particular root growth characteristic(s), identifying a growth characteristic of interest, and then detecting a microbe resident on the plant or plant root, thereby screening for unknown microbes that affect plant root growth. In such instances, the techniques include positioning a plurality of sensors (e.g., conductor plate 126 or parallel conductor plate 626) around a soil location, planting a first seed in the soil location, after the first seed has grown into a first plant having a first plant root, and after a plant-microbe interaction is established between the first plant and a first microbe, receiving data representing a root presence from the sensors (e.g., conductor plate 126 or parallel conductor plate 626) of the plurality sensors, determining a first root growth characteristic of the first plant root based on the data, and identifying the first microbe. In some examples, the technique further includes determining the effect of the first microbe on plant root growth characteristics. A variety of techniques can be used to identify a microbe of the present disclosure, including without limitation detection of nucleic acids by PCR, direct sequencing (e.g., DNA- or RNA-seq), and the like; microscopic and/or histological examination of the microbe; and so forth.

The techniques described above may find use in studying a variety of plant-microbe interactions. In some examples, the microbe is a bacterium. In other examples, the microbe is a fungus. It should be appreciated that the methods for determining an effect of a plan-microbe interaction on a root growth characteristic of the present disclosure can find use for a variety of bacterial or fungal microbes, as well as combinations thereof. In some examples, the plant-microbe interaction are beneficial to the plant (e.g., as with rhizobia or mycorrhizal fungi). In some examples, the plant-microbe interaction are detrimental to the plant (e.g., as with a pathogenic microbe). Examples of pathogenic plant microbes include those of the genera *Xanthomonas, Erwinia, Burkholderia, Pseudomonas, Sclerophthera, Fusarium, Pythium, Achlya, Alternaria, Rhizoctonia, Sarocladium, Thanatephorus, Sclerotium, Sclerotinia, Curvularia, Microdochium, Cochliobolus, Cercospora, Curtobacterium, Ralstonia, Peronospora, Pyricularia, Clavibacter, Agrobacterium, Xylella, Uromyces, Stemphylium, Verticillium, Coprinus, Aphanomyces, Phytophthora, Septoria, Passalora, Colletotrichum, Exserhilum, Macrophomina, Bipolaris, Claviceps, Ramulispora, Gloeocercospora, Phialophora, Diaporthe, Phoma, Puccinia, Tilletia, Ustilago, Urocystis, Erysiphe, Mycosphaerella, Leptosphaeria, Pyrenophora, Calonectria, Gaeumannomyces, Pseudocercosporella*, and so forth. In some examples, the plant 140 is a row crop. In some examples, the plant 140 is maize, soybean, rice, wheat, sorghum, tomato, or alfalfa. Other row crops include, without limitation, cotton, beets, grain hay, legumes (e.g., beans, peanuts, peas, etc.), flowers such as sunflowers, other grains (e.g., rye or oats), sugarcane, tobacco, kenaf, and the like.

In some examples, a plant-microbe interaction is established after a known or hypothesized interaction during contact between a plant 140 or seed 540 of the present disclosure and a microbe of the present disclosure. In some examples, a plant-microbe interaction is established after a particular phenotype of the plant or plant root 142 is observed, such as a visible effect on the plant itself (e.g., change in coloration, above-ground growth, appearance of blight, wilt, or other trait, increased growth in the case of beneficial plant-microbe interactions, and so forth).

As described above, the techniques of a non-invasive root phenotyping devices 100, 600, 1100 of the present disclosure can find use in techniques for monitoring a soil organism. In some examples, the techniques include positioning a plurality of sensors (e.g., conductor plate 126 or parallel conductor plate 626) around a soil location, planting a seed 540 in the soil location, receiving data representing a root presence in contact with or proximity to a conductor plate 126 of the plurality (after the seed has grown into a plant 140 having a plant root 142, and after the soil organism has invaded the soil location), based on the data, determining whether the detected root presence is from the plant root 142 or the soil organism, and in accordance with a determination that the detected root presence is from the soil organism: monitoring the soil organism based on the data. In other examples, the techniques include positioning a plurality of sensors (e.g., conductor plate 126 or parallel conductor plate 626) around a soil location (a plant having a plant root is planted in the soil location, and the soil organism has invaded the soil location), receiving data representing a root presence in contact with or in proximity to a conductor plate 126 of the plurality, based on the data, determining whether the detected root presence is from the plant root or the soil organism, and in accordance with a determination that the detected root presence is from the soil organism: monitoring the soil organism based on the data. In some examples, a type of soil organism is monitored (e.g., the type of soil organism is inferred from its size). In some examples, the soil organism's size is inferred based on, at least in part on, the duration of the signal response 1234 and/or the magnitude of the signal response. In some examples, a number of soil organism(s) of interest are monitored (e.g., based on one or more of duration of the signal response 1234, a signal response 1234 magnitude, and a number of detected roots 142). For example, a number of a particular organism (e.g., corn root worm) in a specific location can be used to decide when to treat with a pesticide, the amount of pesticide to be used, and so forth.

The transient processes such as soil organism contacts can be distinguished from root traits based on a number of aspects. For example, in some instances, the data includes information identifying the magnitude of the signal response. In some examples, the determination that a detected root is from the soil organism is based, at least in part, on the signal response magnitude. In some examples, the data include information identifying duration of a detected root at one or more the sensors (e.g., conductor plate 126 or parallel conductor plate 626). In some examples, the determination that a detected root is from the soil organism is based, at least in part, on the duration of the detected root In some instances, the determination that the detected root is from the soil organism is based on the magnitude of the signal response and the duration of the detected root. It should be appreciated that combination of aspects of the data, such as magnitude and duration, can be used to determine whether the detected root is from a plant root 142 or a soil organism.

In some examples, in accordance with a determination that the detected root is not from the soil organism, the data is stored and/or filtered. For example, in some instance, a further determination is made as to whether the data represent noise/baseline signal or whether the data represent the presence of a plant root 142. In some examples, in accordance with a determination that the data represent noise/baseline signal, the data is filtered. In some examples, in accordance with a determination that the data represent a true presence of a plant root, the data is stored in computer readable medium/memory 408 and/or conditioned (e.g., signal processor 412. This provides tracking of both plant roots 142 and transient inputs from soil organisms.

In some examples, the soil organism is a worm or insect. In some examples, the soil organism is an agricultural pest. In some examples, the soil organism is a corn root worm (e.g., *Diabrotica virgifera*). In some examples, the plant 142 is a row crop. In some examples, the plant 140 is maize, soybean, rice, wheat, sorghum, tomato, or alfalfa. Other row crops include, without limitation, cotton, beets, grain hay, legumes (e.g., beans, peanuts, peas, etc.), flowers such as sunflowers, other grains (e.g., rye or oats), sugarcane, tobacco, kenaf, and the like.

It is understood that the specific order or hierarchy of blocks in the processes/flowcharts disclosed is an illustration of exemplary approaches. Based upon design preferences, it is understood that the specific order or hierarchy of blocks in the processes/flowcharts may be rearranged. Further, some blocks may be combined or omitted. The accompanying method claims present elements of the various blocks in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, hut they are to be accorded the full scope consistent with the language claims, wherein reference to an element in the singular is not intended to mean "one and only one" unless specifically so stated, but rather "one or more." Unless specifically stated otherwise, the term "some" refers to one or more. Combinations such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, where any such combinations may contain one or more member or members of A, B, or C. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. The word "exemplary" is used herein to mean "serving as an example, instance, or illustration." Any example described herein as "exemplary" is not necessarily to be construed as preferred or advantageous over other examples. The words "module," "mechanism," "element," "device," and the like may not be a substitute for the word "means." As such, no claim element is to be construed under 35 U.S.C § 112(f) unless the element is expressly recited using the phrase "means for."

What is claimed is:

1. An electronic device for monitoring growth of a root of a plant in a soil location, comprising:
   a support structure suitable for arrangement adjacent to the soil location; and
   a plurality of electronic sensors affixed to the support structure, wherein at least one electronic sensor of the plurality of electronic sensors comprises:
   a first conductor plate configured to be disposed in soil;
   a switch electrically coupled to the first conductor plate, wherein the switch is configured to switch between a first mode and a second mode;
   a power supply electrically coupled to the switch, wherein the power supply is configured to provide a first electrical charge to the first conductor plate in the first mode of the switch; and
   a signal extractor electrically coupled to the switch, wherein, in the second mode of the switch, the signal extractor is configured to extract a signal at the first conductor plate based on the first electrical charge provided to the first conductor plate in the first mode of the switch.

2. The electronic device of claim 1, further comprising:
   a microcontroller electrically coupled to the signal extractor, wherein the microcontroller is configured to receive the signal from the signal extractor; and
   a memory electrically coupled to the microcontroller, wherein the memory is configured to store data associated with the signal extractor.

3. The electronic device of claim 2, wherein the signal is stored in the memory at predetermined intervals.

4. The electronic device of claim 2, wherein the switch is a multiplexer that is electrically coupled to and controlled by the microcontroller.

5. The electronic device of claim 2, wherein the microcontroller is configured to:
   retrieve a baseline signal from memory; and
   compare the signal to the baseline signal to determine whether a difference between a portion of the signal and a portion of the baseline signal exceeded a threshold value.

6. The electronic device of claim 2, further comprising:
   a second conductor plate configured to be disposed in soil adjacent to and substantially parallel to the first conductor plate, wherein the second conductor plate is electrically coupled to ground.

7. The electronic device of claim 6, wherein a root presence is associated with a determination that the signal exceeded a threshold value.

8. The electronic device of claim 6, wherein the baseline signal is representative of a signal of the electronic sensor in soil without a root disposed between the first conductor plate and the second conductor plate or without a root that is in contact with either the first conductor plate or the second conductor plate.

9. The electronic device of claim 6, wherein a gap between the first conductor plate and the second conductor plate has a cross sectional area of less than or equal to about 1 cm$^2$.

10. The electronic device of claim 6, wherein a distance between the first conductor plate and the second conductor plate is equal to or greater than about 1 mm.

11. The electronic device of claim 6, further comprising a polarity switch configured to exchange electrical coupling between the first conductor plate and the second conductor plate.

12. The electronic device of claim 2, further comprising a soil humidity sensor or a temperature sensor electrically coupled to the microcontroller.

13. The electronic device of claim 1, wherein the signal extractor is a voltage divider or an analog to digital converter.

14. The electronic device claim 1, wherein the support structure comprises a stake or an auger.

15. A method for monitoring growth of a plant root at an electronic device comprising one or more processors, memory, and a plurality of sensors positioned adjacent to the plant root, the method comprising:
   electrically charging, at a sensor among the plurality of sensors, a first conductor plate from a power supply over a first predetermined time, wherein the first conductor plate is configured to be disposed in soil;
   electrically uncoupling the first conductor plate from the power supply;
   extracting a signal at the first conductor plate over a second predetermined time based on the electrical charge provided to the first conductor plate;
   determining whether a portion of the signal exceeds a threshold value, wherein a root presence is associated with a determination that the portion of the signal exceeded the threshold value; and
   storing a root presence indicator to the memory in accordance with the portion of the signal exceeding the threshold value.

16. The method of claim 15, further comprising: electrically grounding a second conductor plate, wherein the second conductor plate is configured to be disposed in soil and adjacent to and substantially parallel to the first conductor plate.

17. The method of claim 15, further comprising: determining one or more of:
   (a) root growth rate, wherein the root growth rate is proportional to a three-dimensional coordinate of the sensor over an elapsed time;
   (b) biomass of the plant root, wherein the biomass is proportional to a magnitude of the signal response;
   (c) biomass growth rate, wherein the biomass growth rate is proportional to the change in biomass over an elapsed time; and
   (d) root angle of the plant root, wherein the root angle is based on an angle between a point of origin of the plant root and a three-dimensional coordinate of the sensor.

18. A non-transitory, computer-readable storage medium comprising one or more programs for execution by one or more processors of an electronic device, the one or more programs including instructions which, when executed by the one or more processors, cause the device to:
   electrically charge, at a sensor among a plurality of sensors, a first conductor plate from a power supply over a first predetermined time, wherein the first conductor plate is configured to be disposed in soil;
   electrically uncouple the first conductor plate from the power supply;
   extract a signal at the first conductor plate over a second predetermined time based on the electrical charge provided to the first conductor plate;
   determine whether a portion of the signal exceeds a threshold value, wherein a root presence is associated with a determination that the portion of the signal exceeded the threshold value; and
   store a root presence indicator to a memory in accordance with the portion of the signal exceeding the threshold value.

19. The non-transitory, computer-readable storage medium of claim 18, wherein the instructions which, when executed by the one or more processors, further causes the device to:
   electrically ground a second conductor plate, wherein the second conductor plate is configured to be disposed in soil and adjacent to and substantially parallel to the first conductor plate.

20. The non-transitory, computer-readable storage medium of claim 18, wherein the instructions which, when executed by the one or more processors, further cause the device to:
   determine one or more of:
   (a) a root growth rate, wherein the root growth rate is proportional to a three-dimensional coordinate of the sensor over an elapsed time;
   (b) biomass of the plant root, wherein the biomass is proportional to a magnitude of the signal response;
   (c) biomass growth rate, wherein the biomass growth rate is proportional to the change in biomass over an elapsed time; and
   (d) root angle of the plant root, wherein the root angle is based on an angle between a point of origin of the plant root and a three-dimensional coordinate of the sensor.

21. The electronic device of claim 1, wherein the support structure is a lateral support onto which the plurality of electronic sensors is affixed.

22. The electronic device of claim 21, wherein the plurality of electronic sensors is affixed to the lateral support between two extended vertical supports.

23. The electronic device of claim 1, wherein the support structure is made from plastic.

24. The electronic device of claim 2, wherein the device comprises a microcontroller that is removable from the device.

25. The electronic device of claim 2, wherein the device further comprises a communications unit configured to transmit data.

26. The electronic device of claim 25, wherein the communications unit is removable from the device.

27. A method for monitoring growth of a plant root at two electronic devices, both of which comprise one or more processors, memory, and a plurality of sensors positioned adjacent to the plant root, the method comprising monitoring growth of the plant root according to the method of claim 15 at each of the electronic devices, wherein the electronic devices are positioned on either side of the plant root.

28. The method of claim 27, wherein the plant is a row crop.

* * * * *